(12) United States Patent
Kocher et al.

(10) Patent No.: US 11,981,962 B2
(45) Date of Patent: May 14, 2024

(54) METHODS AND MATERIALS FOR THE EFFECTIVE USE OF COMBINED TARGETED ENRICHMENT OF GENOMIC REGIONS AND LOW COVERAGE WHOLE GENOME SEQUENCING

(71) Applicant: Mayo Foundation for Medical Education and Research, Rochester, MN (US)

(72) Inventors: Jean-Pierre A. Kocher, Rochester, MN (US); Chen Wang, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 575 days.

(21) Appl. No.: 16/310,171

(22) PCT Filed: Jun. 16, 2017

(86) PCT No.: PCT/US2017/037819
§ 371 (c)(1),
(2) Date: Dec. 14, 2018

(87) PCT Pub. No.: WO2017/218864
PCT Pub. Date: Dec. 21, 2017

(65) Prior Publication Data
US 2019/0177786 A1    Jun. 13, 2019

Related U.S. Application Data

(60) Provisional application No. 62/351,742, filed on Jun. 17, 2016.

(51) Int. Cl.
*C12Q 1/6869*    (2018.01)
*C12Q 1/6806*    (2018.01)
(Continued)

(52) U.S. Cl.
CPC ......... *C12Q 1/6869* (2013.01); *C12Q 1/6806* (2013.01); *C12Q 1/686* (2013.01);
(Continued)

(58) Field of Classification Search
CPC .... C12Q 1/6869; C12Q 1/6806; C12Q 1/686; C12Q 1/6876; C12Q 1/6886; G16B 20/00;
(Continued)

(56) References Cited

U.S. PATENT DOCUMENTS 11,274,343 B2 *  3/2022  Jarosz ................. C12Q 1/6874
2015/0110754 A1   4/2015  Bai et al.
(Continued)

FOREIGN PATENT DOCUMENTS

WO  WO-2015051275 A1 *  4/2015  ....... G06F 16/24578
WO  WO-2016123692 A1 *  8/2016  ........ B01L 3/502761
WO  WO-2016209703 A1 * 12/2016  ........... C12Q 1/6886

OTHER PUBLICATIONS

Spencer et al. (The Journal of Molecular Diagnostics, 2014, vol. 16, No. 1, pp. 75-88) (Year: 2014).*
(Continued)

*Primary Examiner* — Jeremy C Flinders
(74) *Attorney, Agent, or Firm* — Fish & Richardson P.C.

(57) ABSTRACT

This document provides methods and materials for using low coverage whole genome sequencing techniques to assess genomes. For example, methods and materials for using targeted nucleic acid amplification and/or capture techniques in combination with low coverage whole genome sequencing techniques to obtain high coverage sequencing data for one or more pre-selected regions of a genome are provided.

12 Claims, 5 Drawing Sheets
Specification includes a Sequence Listing.

(51) Int. Cl.
  *C12Q 1/686*   (2018.01)
  *C12Q 1/6876*  (2018.01)
  *C12Q 1/6886*  (2018.01)
  *G16B 20/00*   (2019.01)
  *G16B 20/20*   (2019.01)
  *G16B 25/00*   (2019.01)
  *G16B 25/20*   (2019.01)
  *G16B 30/00*   (2019.01)

(52) U.S. Cl.
  CPC ......... *C12Q 1/6876* (2013.01); *C12Q 1/6886* (2013.01); *G16B 20/00* (2019.02); *G16B 20/20* (2019.02); *G16B 25/00* (2019.02); *G16B 25/20* (2019.02); *G16B 30/00* (2019.02)

(58) Field of Classification Search
  CPC ........ G16B 20/20; G16B 25/00; G16B 25/20; G16B 30/00
  See application file for complete search history.

(56) References Cited

U.S. PATENT DOCUMENTS

2015/0307929 A1   10/2015   Leamon et al.
2016/0122817 A1    5/2016   Jarosz et al.

OTHER PUBLICATIONS

Extended European Search Report in European Appl. No. 17814148.7 dated Jun. 24, 2019, 9 pages.
Hagemann et al., "Design of targeted, capture-based, next generation sequencing tests for precision cancer therapy," Cancer Genetics, 206(12):420-431, Dec. 2013.
International Search Report & Written Opinion in International Application No. PCT/US2017/037819 dated Oct. 6, 2017, 9 pages.
Kuilman et al., "CopywriteR: DNA copy number detection from off-target sequence data" Genome biology, 16(1):49, Feb. 2015.
Pasaniuc et al., "Extremely low-coverage sequencing and imputation increases power for genome-wide association studies," Nature genetics, 44(6):631, Jun. 2012.
Simon et al., "Using formaldehyde-assisted isolation of regulatory elements (FAIRE) to isolate active regulatory DNA," Nature protocols, 7(2):256, Feb. 2012.
Spencer et al., "Comparison of Clinical Targeted Next-Generation Sequence Data from Formalin-Fixed and Fresh-Frozen Tissue Specimens," J. Mol. Diagn., Sep. 2013, 15(5):623-633.

\* cited by examiner

METHODS AND MATERIALS FOR THE EFFECTIVE USE OF COMBINED TARGETED ENRICHMENT OF GENOMIC REGIONS AND LOW COVERAGE WHOLE GENOME SEQUENCING

CROSS-REFERENCE TO RELATED APPLICATIONS

This application is a National Stage application under 35 U.S.C. § 371 of International Application No. PCT/US2017/037819, having an International Filing Date of Jun. 16, 2017, which claims priority to U.S. Application Ser. No. 62/351,742, filed on Jun. 17, 2016. The disclosures of the prior applications are considered part of the disclosure of this application, and are incorporated in their entirety into this application.

SEQUENCE LISTING

This application contains a Sequence Listing that has been submitted electronically as an ASCII text file named 1560US1_ST25.txt. The ASCII text file, created on Jun. 16, 2017, is 47 kilobytes in size. The material in the ASCII text file is hereby incorporated by reference in its entirety.

BACKGROUND

1. Technical Field

This document relates to methods and materials involved in using low coverage whole genome sequencing (LC-WGS) techniques to assess genomes. For example, this document provides methods and materials for performing targeted enrichment of genomic regions (e.g., targeted amplification and/or targeted capture techniques) in combination with LC-WGS techniques to assess genomes.

2. Background Information

High coverage whole genome sequencing techniques, which could theoretically be used to call variants, amplifications, and deletions genome wide, is currently not used in clinical applications due to the high cost of the test as well as the complexity of interpreting results. One whole genome sequencing assay used for clinical application is the LC-WGS assay that has a coverage of about 1× or less. LC-WGS was used successfully for the non-invasive screening of fetuses to report trisomy of chromosome 13, 18, and 21.

SUMMARY

This document provides methods and materials for using low coverage whole genome sequencing techniques to assess genomes. For example, this document provides methods and materials for using targeted nucleic acid amplification and/or targeted nucleic acid capture techniques in combination with low coverage whole genome sequencing techniques to obtain high coverage sequencing data for one or more pre-selected regions of a genome. Generally, during whole genome sequencing, DNA is fragmented into short fragments that are about 400 to 500 base pairs long. About 100 to 150 base pairs are sequenced at one or both ends of these fragments. A sequenced section of a DNA fragment is called a sequence read. Coverage refers to the number of reads spanning over a specific genomic location. A sample sequenced at 10× average coverage means that, on average, 10 reads span the genomic regions that were sequenced.

As described herein, combining targeted nucleic acid amplification and/or targeted nucleic acid capture techniques with low coverage whole genome sequencing techniques can generate a sequencing coverage that is less than about 1× for the regions of the genome outside the one or more pre-selected regions amplified and/or captured and a sequencing coverage that is greater than about 500× for the one or more pre-selected regions. For example, combining targeted nucleic acid amplification and/or targeted nucleic acid capture techniques with low coverage whole genome sequencing can provide a composite low resolution view of genomic variations across the genome with a high resolution view of genomic variations in one or more selected regions that were enriched via nucleic acid amplification and/or nucleic acid capture techniques. This can allow clinicians to obtain high coverage sequencing data for one or more pre-selected regions of a genome while performing cost effective, low coverage whole genome sequencing.

In general, one aspect of this document features a method for increasing the number of sequencing reads of one or more pre-selected genomic regions using low coverage whole genome sequencing. The method comprises, or consist essentially of, performing an amplification reaction using a genomic nucleic acid sample to amplify one or more pre-selected genomic regions, thereby forming an amplified sample, and performing low coverage whole genome sequencing using the amplified sample, wherein the coverage of the pre-selected genomic regions using the low coverage whole genome sequencing is greater than 250×, and wherein the coverage of regions outside the pre-selected genomic regions using the low coverage whole genome sequencing is less than 10×, less than 5×, or less than 3×. The one or more pre-selected genomic regions can be from one pre-selected genomic region to 2500 pre-selected genomic regions. The one or more pre-selected genomic regions can be from one pre-selected genomic region to 2000 pre-selected genomic regions. The one or more pre-selected genomic regions can be from one pre-selected genomic region to 1500 pre-selected genomic regions. The low coverage whole genome sequencing can be whole genome sequencing with less than 2× genome wide coverage. The low coverage whole genome sequencing can be whole genome sequencing with less than 1× genome wide coverage. The genomic nucleic acid sample can be a human genomic nucleic acid sample. The coverage of the pre-selected genomic regions using the low coverage whole genome sequencing can be greater than 500×. The coverage of the pre-selected genomic regions using the low coverage whole genome sequencing can be greater than 1000× (or greater than 1500×, greater than 2000×, greater than 3000×, greater than 5000×, greater than 7500×, or greater than 10000×). The method can comprise performing the amplification reaction using the genomic nucleic acid sample to amplify one or more pre-selected genomic regions having a length from about 150 bp to about 750 bp.

In another aspect, this document features a method for increasing the number of sequencing reads of one or more pre-selected genomic regions using low coverage whole genome sequencing. The method comprises, or consists essentially of, performing a nucleic acid capture reaction using a genomic nucleic acid sample to enrich one or more pre-selected genomic regions, thereby forming an enriched sample, and performing low coverage whole genome sequencing using the enriched sample, wherein the coverage of the pre-selected genomic regions using the low coverage whole genome sequencing is greater than 250×, and wherein the coverage of regions outside the pre-selected genomic regions using the low coverage whole genome sequencing is less than 10×, less than 5×, or less than 3×. The one or more pre-selected genomic regions can be from one pre-selected genomic region to 2500 pre-selected genomic regions. The one or more pre-selected genomic regions can be from one pre-selected genomic region to 2000 pre-selected genomic regions. The one or more pre-selected genomic regions can be from one pre-selected genomic region to 1500 pre-selected genomic regions. The low coverage whole genome sequencing can be whole genome sequencing with less than 2× genome wide coverage. The low coverage whole genome sequencing can be whole genome sequencing with less than 1× genome wide coverage. The genomic nucleic acid sample can be a human genomic nucleic acid sample. The coverage of the pre-selected genomic regions using the low coverage whole genome sequencing can be greater than 500×. The coverage of the pre-selected genomic regions using the low coverage whole genome sequencing can be greater than 1000× (or greater than 1500×, greater than 2000×, greater than 3000×, greater than 5000×, greater than 7500×, or greater than 10000×). The method can comprise performing the nucleic acid capture reaction using the genomic nucleic acid sample to capture one or more pre-selected genomic regions having a length from about 150 bp to about 750 bp.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials for using low coverage whole genome sequencing techniques to assess genomes (e.g., genomic variations). For example, this document provides methods and materials for using targeted nucleic acid amplification and/or targeted nucleic acid capture techniques in combination with low coverage whole genome sequencing techniques to obtain high coverage sequencing data (e.g., over 500× coverage) for one or more selected regions of a genome.

Figure 2:
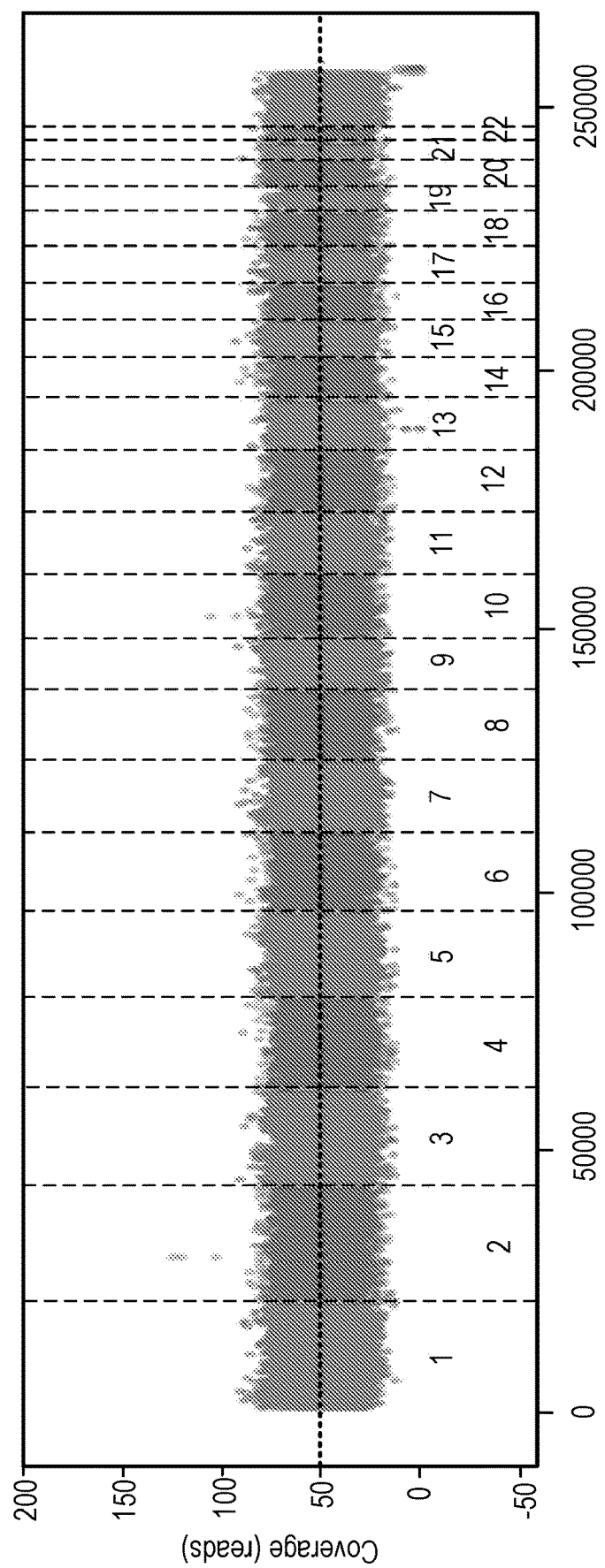
FIG. 2 is a graph plotting LC-WGS sequencing coverage of a normal sample. The X axis displays the coverage on each chromosome that are numbered in ascending order. The Y axis is the number of reads mapped to the genomic region associated to a bin. Bioinformatics techniques are applied to the data to optimize evenness of coverage across the genome (X axis). Each dot on the plot represents a bin of 10 kb. In this example, bins include in average 50 reads, but fluctuate between 10× and 80×. In this sample, no statistically significant amplifications or deletions are observed.

Low coverage whole genome sequencing can be performed by limiting the concentration of DNA input in the sequencing reaction. A sample from a healthy human and assessed using low coverage whole genome sequencing without enriching pre-selected regions can be as shown in FIG. 2. In some cases, samples can be multiplexed in a single whole genome sequencing assay. The concentration of each sample can be controlled to ensure that the DNA concentration is proportional to the number of samples. For example, the Illumina HiSeq 2000 can be set to produce per lane of flow cell: 300,000,000 reads that are 100 base pair long. Since the human genome is about 3 billion bases long, the whole genome of a single sample could be sequenced with a coverage of 10× coverage. If 10 samples are sequenced together in a flow cell lane, then the coverage per sample will be on average about 1×.

Figure 3:
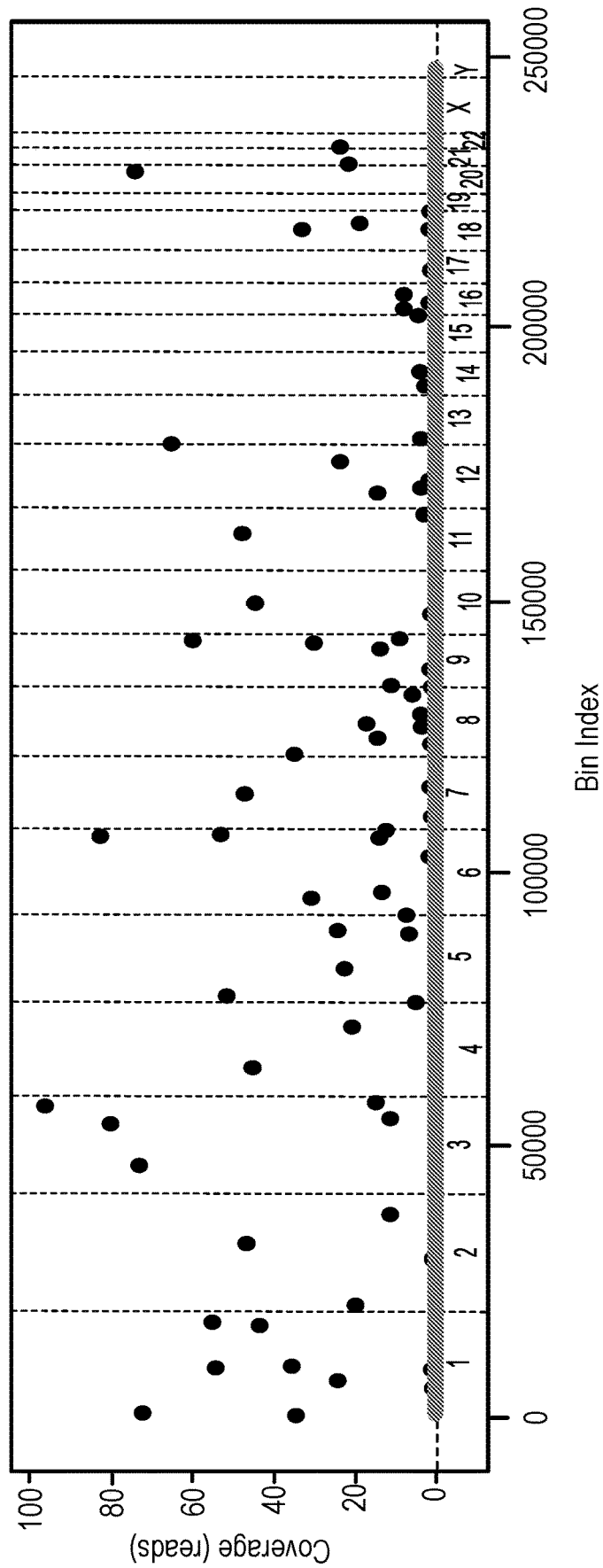
FIG. 3 is a graph plotting the sequencing results obtained by combining the use of low coverage whole genome sequencing and amplification of selected regions. The X axis displays the coverage on each chromosome that are numbered in ascending order. The Y axis is the number of reads divided by 1000 that are mapped to the genomic region associated to a bin. The sample sequenced is a normal sample. Each circle represents a bin of 10 kb. The LC-WGS is represented by set of grey circles that form a base line due to the scale of the plot. On average, 50 reads of 150 bp are found in each bin. The black circles represent the coverage level of 97 loci that are 90 bases long and that were amplified using a PCR assay (amplicon). The coverage of these loci can reach for some of them 100,000× and therefore can be used to call genotypes, identify somatic mutations, identify breakpoints associated to structural variants or identify change of coverage informative of the amplification or deletion of these regions. In this example, the amplified regions overlap with SNPs from which the genotypes can be called accurately. The genotypes of SNPs cannot be called from low coverage sequencing alone.

As described herein, combining targeted nucleic acid amplification and/or capture techniques with low coverage whole genome sequencing techniques can generate a sequencing coverage that is from less than about 1× coverage for the regions of the genome outside the one or more selected regions amplified and/or captured and a sequencing coverage that can be greater than 50,000× for the one or more selected regions (see, e.g., FIG. 3).

Any appropriate nucleic acid amplification technique can be used to increase the sequence read coverage of one or more selected regions targeted for amplification. For example, PCR amplification can be used to increase the sequence read coverage of one or more selected regions when low coverage whole genome sequencing is used. In some cases, nucleic acid amplification techniques can be used to amplify more than 2000 regions of a genome. Increasing the number of amplified regions decreases the number of reads available to cover the whole genome and therefore decreases the LC-WGS coverage.

In some cases, nucleic acid capture techniques can be used in addition to, or in place of, nucleic acid amplification techniques to increase the sequence read coverage of one or more selected regions targeted for enrichment. Any appropriate nucleic acid capture technique can be used to increase the sequence read coverage of one or more selected regions targeted for enrichment. For example, DNA can be used as bait to capture a targeted sequence as described elsewhere (Hagemann et al., *Cancer Genetics,* 206:420-431 (2014)).

In some cases, in a single experimental protocol, a low coverage whole genome sequencing assay can be combined with a targeted amplicon assay, where PCR is used to amplify selected regions of the genome. In some cases, the amplification step can be replaced with a nucleic acid capture technique to capture genomic regions that can be combined with a low coverage whole genome sequencing assay. The sequencing result can be a combination of low coverage whole genome sequencing that provides an overview of the genomic amplification/deletion (e.g., duplications or other genomic amplifications or genomic deletions) landscape of the genome with high coverage sequencing data for the amplified and/or captured regions (e.g., a coverage up to several 1000×; see, e.g., FIG. 3). This high coverage sequencing data obtained using an otherwise low coverage whole genome sequencing assay can be used to identify single nucleotide variants, indels, translocations, and/or copy number changes at a high sensitivity. For example, selected genomic regions can be selected and enriched (e.g., amplified) so that high coverage is obtained for those regions to identify SNPs, genomic amplifications, genomic deletions, and translocations. In some cases, the high sensitivity in these regions can be set to be similar to that obtained using fluorescence in situ hybridization (FISH) techniques.

Figure 1:
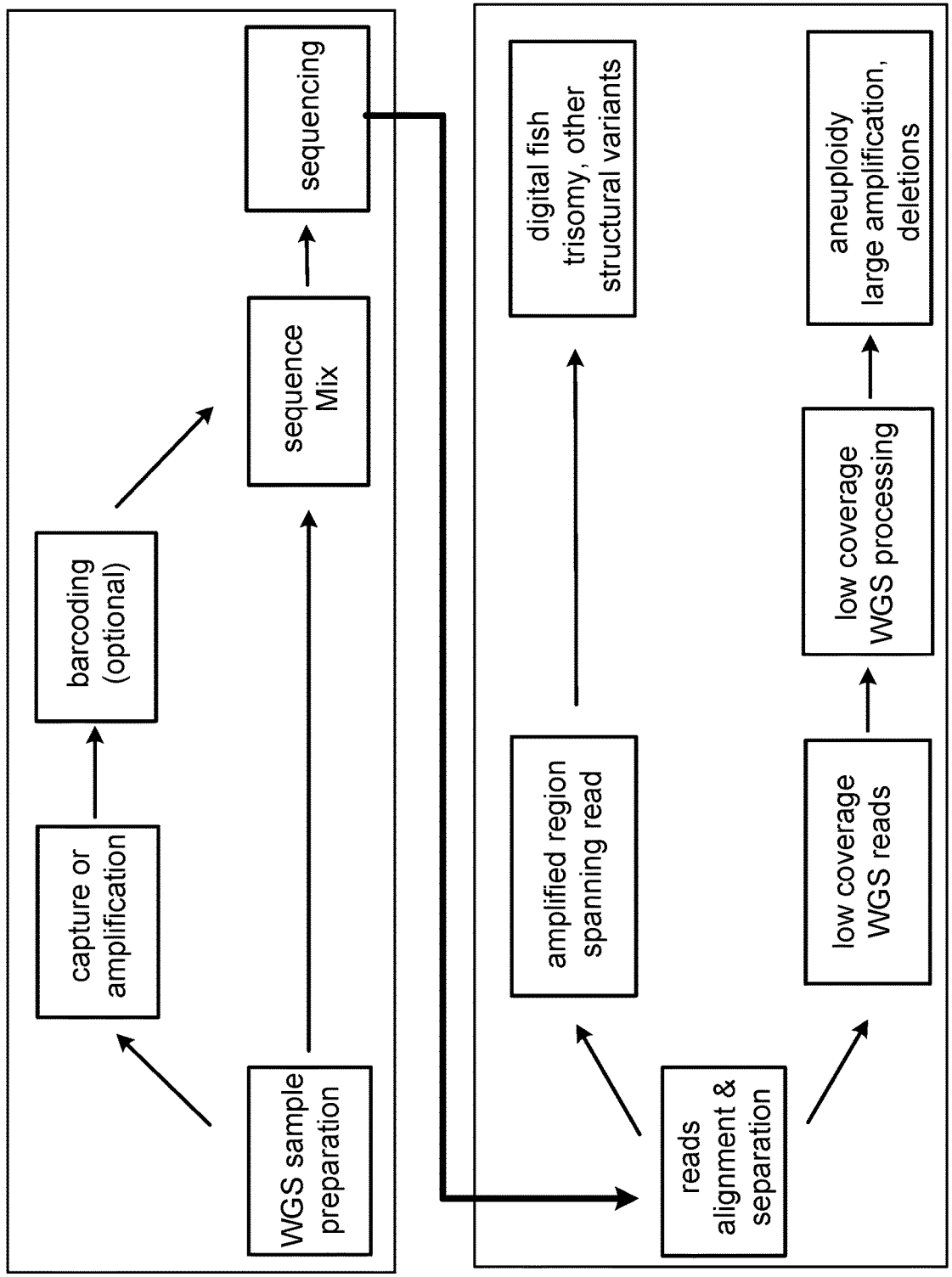
FIG. 1 is a schematic of the steps of an exemplary workflow for the processing of a sequencing protocol according to one embodiment.

Briefly, one exemplary implementation of the methods provided herein can include the following steps: (a) DNA extraction, (b) an optional whole genome amplification step if enough DNA is not available, (c) PCR amplification of one or more targeted genomic regions with a controlled number of PCR cycles, (d) optional genomic barcoding if multiple samples are to be sequenced in a single experiment, and (e) low coverage whole genome sequencing. Other exemplary implementations of the methods provided herein can be carried out as set forth in FIG. 1.

Since the amount of DNA sequenced is about constant per sequencing experiment, the number and length of the genomic regions to be amplified, the coverage level expected for these regions, and the number of samples to be sequenced in a single experiment can be directly related to the sequencing reads left to cover the whole genome.

The following parameters can be used to design an assay provided herein such that it achieves a particular coverage for the genomic regions enriched and those genomic regions not enriched: (a) total number of reads produced by the sequencing platform, (b) number of samples to sequence in a single experiment, (c) number of target regions to amplify or capture, (d) length of the region to amplified or captured, and (e) expected coverage of the enriched target regions.

The following defines the relationship between these parameters:

$$LC = (RS*RL - AN*AL*AC)/LG$$

where:
RS is the number of sequenced read per sample
RL is the length of a read (in bases)
AN is the number of amplicons
AL is the length of the amplicons (in bases)
AC is the coverage of each amplicons
LC is the coverge of the LC-WGS
LG is the number of base pair in the sequenced genome Table 1 sets forth different exemplary combinations of the parameters RL, AN, AL, AC, and LC. LG is set to 3 billion base pairs (human genome)

TABLE 1

| reads per sample (RS) | read length (RL) | number of amplicons (AN) | amplicon length (AL) | amplicon coverage (AC) | LC-WGS coverage (LC) |
|---|---|---|---|---|---|
| 30,000,000 | 100 | 100 | 500 | 5,000 | 0.92 |
| 30,000,000 | 100 | 100 | 1000 | 5,000 | 0.83 |
| 30,000,000 | 150 | 200 | 500 | 5,000 | 1.33 |
| 30,000,000 | 150 | 200 | 1000 | 5,000 | 1.17 |
| 40,000,000 | 150 | 200 | 500 | 10,000 | 1.67 |
| 40,000,000 | 150 | 200 | 1000 | 10,000 | 1.33 |
| 40,000,000 | 150 | 300 | 500 | 10,000 | 1.50 |
| 40,000,000 | 150 | 300 | 1000 | 10,000 | 1.00 |

In some cases, the methods and materials provided herein can be used for the early detection of cancer or to stratify tumors on the basis of, for example, genome wide aneuploidy events and, in the target enriched regions: copy number alterations, mutations, and diverse structural variants. In some cases, the methods and materials provided herein can be used to monitor recurrence of cancer following treatment (e.g., surgery) with the enriched (e.g., amplified and/or captured) selected regions being selected based on the SNPs or translocations of the original tumor.

Any appropriate genome can be assessed using the methods and materials provided herein. For example, the genome of a human, horse, bovine species, dog, cat, or monkey can be assessed using the methods and materials provided herein. In addition, any appropriate sample containing genomic nucleic acid can be used as described herein. For example, the methods and materials provided herein can be used to analyze DNA extracted from cells or cell-free DNA extracted from blood, from brushings, or tampons. In some cases, the methods and materials described herein can be used to assess nucleic acid from fresh samples, frozen samples, or formalin-fixed paraffin embedded samples. Any appropriate sample preparation technique can be used to extract DNA from cells or extract cell-free DNA from blood, feces, urine, tampons, or brushing samples. For example, a nucleic acid extraction kits can be used.

Any appropriate genome region can be a selected target region that is amplified or enriched to increase its sequence read coverage during low coverage whole genome sequencing. For example, any one or more of the nucleic acid regions set forth in Table 2 (or portions thereof) can be amplified as described herein to generate amplified selected regions that provide an increased sequence read coverage during low coverage whole genome sequencing. Such nucleic acid regions can be used to detect a genetic defect or element within the amplified regions.

TABLE 2

Exemplary selected regions of human genome for amplification or capture enrichment.

| Gene | Chr | Exon | Exon Start | Exon End | Primer Start | Primer End | Len | Fwd Primer | SEQ ID NO: | Rev Primer | SEQ ID NO: | ID |
|---|---|---|---|---|---|---|---|---|---|---|---|---|
| CCND1 | chr11 | 1 | 69455872 | 69456279 | 69455842 | 69456390 | 549 | GGCTTTGATCTTTGCTTAAC | 9 | AAACTTCAAAGTTCTAGCGG | 162 | 1 |
| CCND1 | chr11 | 2 | 69457798 | 69458014 | 69457592 | 69458125 | 534 | GGACTTTCCCTTTCAGTTTC | 10 | AGGAGCAGATATGTCAGAGG | 163 | 2 |
| CCND1 | chr11 | 3 | 69458599 | 69458759 | 69458336 | 69458863 | 528 | GGAGGTCTTTTTGTTTCCAC | 11 | GACATCTTCCAGACAGCAC | 164 | 3 |
| CCND1 | chr11 | 4 | 69462761 | 69462910 | 69462512 | 69463092 | 581 | TTCCTTGGTTATGTTTGAGTC | 12 | TCTAGGAGCAGTGGAAGAAG | 165 | 4 |
| CCND1 | chr11 | 5 | 69465885 | 69469242 | 69465779 | 69466337 | 559 | TTGCTCTTATAAAGGCTTCC | 13 | TATCATCTGTAGCACCAAGG | 166 | 5 |
| CCND1 | chr11 | 5 | 69465885 | 69469242 | 69466159 | 69466730 | 572 | AAGCTTCATTCTCCTTGTTG | 14 | ACGTACTGTAACCAAGAGG | 167 | 6 |
| CCND1 | chr11 | 5 | 69465885 | 69469242 | 69466597 | 69467101 | 505 | GCATCTCTGTACTTTGCTTG | 15 | AACAGCGCTATTTCCTACAC | 168 | 7 |
| CCND1 | chr11 | 5 | 69465885 | 69469242 | 69467056 | 69467580 | 525 | ATTTCCAAGCACTTTCAGTC | 16 | AGAAGGTTTGTGTGTGTGTG | 169 | 8 |
| CCND1 | chr11 | 5 | 69465885 | 69469242 | 69467560 | 69468087 | 528 | ACACACACACACACAACCTTC | 17 | CAGCAAACAATGTGAAAGAG | 170 | 9 |
| CCND1 | chr11 | 5 | 69465885 | 69469242 | 69468041 | 69468490 | 450 | GGAAATATTCACATCGCTTC | 18 | ACTACTATGATGCTACGCCC | 171 | 10 |
| CCND1 | chr11 | 5 | 69465885 | 69469242 | 69468254 | 69468737 | 484 | TGTTTCACAATACCTCCATGC | 19 | GATTTGGAGTCTCTTTAAATTAGC | 172 | 14 |
| CCND1 | chr11 | 5 | 69465885 | 69469242 | 69468591 | 69469036 | 446 | ACCTGTAGGACTCTCATTCG | 20 | TCTCGATACACACAACAATCC | 173 | 13 |
| CCND1 | chr11 | 5 | 69465885 | 69469242 | 69469013 | 69469596 | 584 | TCCTGGATGTTGTGTGTATC | 21 | AGCCTGCAAATTATTCTCTG | 174 | 12 |
| LMO1 | chr11 | 1 | 8289973 | 8290182 | 8289734 | 8290333 | 600 | GAGACTTCCTAATCCCGCCG | 22 | CTCTGCTGAGGCCAGTACGG | 175 | 11 |
| LMO1 | chr11 | 2 | 8251837 | 8252051 | 8251723 | 8252126 | 404 | GAGAGGACACACAGGGTACT | 23 | ATTCTTCTGGGGATATTCCTT | 176 | 15 |
| LMO1 | chr11 | 3 | 8248521 | 8248647 | 8248278 | 8248787 | 510 | TATTCACACAGAAATGCC | 24 | TCTTATCCTATTGCCTGAGC | 177 | 16 |
| LMO1 | chr11 | 4 | 8245850 | 8246268 | 8245819 | 8246368 | 550 | AGGTCTGTGTCAGTCATGTG | 25 | ACATAGCTCACCTCATAGGC | 178 | 17 |
| MDM2 | chr12 | 1 | 69201951 | 69202271 | 69201702 | 69202276 | 575 | GGCTAAAGGAGTGTGTCACAGC | 26 | AGTACCTGCTCCTCCACCATC | 179 | 18 |
| MDM2 | chr12 | 2 | 69202987 | 69203072 | 69202745 | 69203311 | 567 | AAGTCCTGACTTGTCTCCAG | 27 | CACGCTTAACAATGTAATGG | 180 | 19 |
| MDM2 | chr12 | 3 | 69207333 | 69207408 | 69207149 | 69207681 | 533 | TGGATTGGATACTGTCTGTG | 28 | ATTCTGGGAAGGAGTCTACC | 181 | 20 |
| MDM2 | chr12 | 4 | 69210591 | 69210725 | 69210331 | 69210882 | 552 | TTAGTAGAGATGGGACCAGG | 29 | GGTTCTCAAATAATATGCCG | 182 | 21 |
| MDM2 | chr12 | 5 | 69214104 | 69214154 | 69213983 | 69214509 | 527 | TTTGAATGTGTGCAGTAGTTC | 30 | TCCTTACACATGTCCTACC | 183 | 22 |

TABLE 2-continued

Exemplary selected regions of human genome for amplification or capture enrichment.

| Gene | Chr | Exon | Exon Start | Exon End | Primer Start | Primer End | Len | Fwd Primer | SEQ ID NO: | Rev Primer | SEQ ID NO: | ID |
|---|---|---|---|---|---|---|---|---|---|---|---|---|
| MDM2 | chr12 | 6 | 69218142 | 69218210 | 69218039 | 69218363 | 325 | AAATTGCATAAGGGTTTGTG | 31 | TTCTCTTCCTGAAGCTCTTG | 184 | 23 |
| MDM2 | chr12 | 7 | 69218334 | 69218431 | 69218161 | 69218640 | 480 | CATCTGTGAGTGAGAACAGG | 32 | GTAAACTGTGCCTGCTGTAG | 185 | 24 |
| MDM2 | chr12 | 8 | 69222550 | 69222711 | 69222304 | 69222899 | 596 | AGATTGTGCCTCTGTACTCC | 33 | ATTTCTCACAATACCTTGGG | 186 | 25 |
| MDM2 | chr12 | 9 | 69229608 | 69229764 | 69229556 | 69230130 | 575 | ACAGAGGTCAAGAGGTGATG | 34 | TGGGAAACAGATCTCTAAGG | 187 | 26 |
| MDM2 | chr12 | 10 | 69230451 | 69230529 | 69230398 | 69230878 | 481 | TCTGATTGAAGGAAATAGGG | 35 | GCCTGTAATTCCAGCTACTC | 188 | 27 |
| MDM2 | chr12 | 11 | 69233053 | 69239324 | 69232933 | 69233478 | 546 | AAACACTGAATATTGAGCCC | 36 | TGACAAATCACACAAGGTTC | 189 | 28 |
| MDM2 | chr12 | 11 | 69233053 | 69239324 | 69233263 | 69233839 | 577 | CAGAGAGTCATGTGTTGAGG | 37 | AGTTGGTGTAAAGGATGAGC | 190 | 29 |
| MDM2 | chr12 | 11 | 69233053 | 69239324 | 69233819 | 69234364 | 546 | AGCTCATCCTTTACACCAAC | 38 | GCTAGATCATGACACTGCAC | 191 | 30 |
| MDM2 | chr12 | 11 | 69233053 | 69239324 | 69234347 | 69234878 | 532 | GCAGTGTCATGATCTAGCAG | 39 | TGAGGTGAGTAGATCACTTGAAG | 192 | 31 |
| MDM2 | chr12 | 11 | 69233053 | 69239324 | 69234715 | 69235284 | 570 | TCTGGGTTCAAGCTATTCTC | 40 | TTTGTCTTACGGGTAAATGG | 193 | 32 |
| MDM2 | chr12 | 11 | 69233053 | 69239324 | 69235142 | 69235665 | 524 | GCTAAGTAGGATTACAGGCG | 41 | GCTTGAGAGGAAGTCAAGAG | 194 | 33 |
| MDM2 | chr12 | 11 | 69233053 | 69239324 | 69235413 | 69235862 | 450 | TAAAGTACCTTCTTGGCCTG | 42 | ACAGAATGCTTAGTCCACC | 195 | 34 |
| MDM2 | chr12 | 11 | 69233053 | 69239324 | 69235711 | 69236286 | 576 | GTGTTAGTTCTTTGGACC | 43 | GTAATCACCTTTCATCGAAG | 196 | 35 |
| MDM2 | chr12 | 11 | 69233053 | 69239324 | 69236212 | 69236802 | 591 | CTCCTTTGGAGACTTAGAACC | 44 | AGCTTGTTCTACCAGGAATG | 197 | 36 |
| MDM2 | chr12 | 11 | 69233053 | 69239324 | 69236522 | 69237080 | 559 | AAGGGAGGATATAAGGAACC | 45 | CTCTCAATAAATGGCCAAAG | 198 | 37 |
| MDM2 | chr12 | 11 | 69233053 | 69239324 | 69237017 | 69237603 | 587 | CCAAATAATGCTTTGAGGAC | 46 | AAAGAGATTCTGCTTGTTG | 199 | 38 |
| MDM2 | chr12 | 11 | 69233053 | 69239324 | 69237424 | 69237893 | 470 | GGACTGAGGTAATTCTGCAC | 47 | CCCATAAACATGTTGAATCC | 200 | 39 |
| MDM2 | chr12 | 11 | 69233053 | 69239324 | 69237579 | 69238177 | 599 | AGCTACAACCAAGCAGAATC | 48 | TGCAACATCATTCTCTCAAG | 201 | 40 |
| MDM2 | chr12 | 11 | 69233053 | 69239324 | 69237775 | 69238260 | 486 | TTTCTGAGGAGTATCGTAGC | 49 | ACCATTCACGATCACTTAGG | 202 | 41 |
| MDM2 | chr12 | 11 | 69233053 | 69239324 | 69238214 | 69238663 | 450 | CTTCTCTTAGGTCACATGGC | 50 | AAGCAGAACCACTTGAACAC | 203 | 42 |
| MDM2 | chr12 | 11 | 69233053 | 69239324 | 69238402 | 69238927 | 526 | TTGTGAGGCACAAATGTAAG | 51 | TTCACAATGCCATTAACAAC | 204 | 43 |
| MDM2 | chr12 | 11 | 69233053 | 69239324 | 69238879 | 69239450 | 572 | GGTCTGTAGGCTTATGATGG | 52 | GAGATGTGGGATTGTAGGAC | 205 | 44 |
| MDM4 | chr1 | 1 | 204485506 | 204485637 | 204485352 | 204485901 | 550 | AAATCTGACGACTTTCAACC | 53 | ACGTCGACTTTAGGTTTGTC | 206 | 45 |

TABLE 2-continued

Exemplary selected regions of human genome for amplification or capture enrichment.

| Gene | Chr | Exon | Exon Start | Exon End | Primer Start | Primer End | Len | Fwd Primer | SEQ ID NO: | Rev Primer | SEQ ID NO: | ID |
|---|---|---|---|---|---|---|---|---|---|---|---|---|
| MDM4 | chr1 | 2 | 204494611 | 204494724 | 204494451 | 204495019 | 569 | AAGATATGCAGAACCTCAGC | 54 | CATAATTCACTGCAGCTTTG | 207 | 46 |
| MDM4 | chr1 | 3 | 204495487 | 204495562 | 204495232 | 204495823 | 592 | AAATTACCTGGATATGGTGG | 55 | GTCAGGAGACTGAGACCATC | 208 | 47 |
| MDM4 | chr1 | 4 | 204499811 | 204499945 | 204499574 | 204500079 | 506 | ATCAGTTCATTTCTGTGCTG | 56 | TGCCTCATAGGCTACCTAAC | 209 | 48 |
| MDM4 | chr1 | 5 | 204501318 | 204501374 | 204501252 | 204501832 | 581 | GGCAAACCACTGATATCTTC | 57 | GAGACATATCAACCAAAGGC | 210 | 49 |
| MDM4 | chr1 | 6 | 204506557 | 204506625 | 204506510 | 204506840 | 331 | ATGGTTATTACCAGGGAAGG | 58 | AGAAGTGCTACATCCCAAAG | 211 | 50 |
| MDM4 | chr1 | 7 | 204507336 | 204507436 | 204507222 | 204507638 | 417 | TTCTTGTGTGTAACCCATTG | 59 | ATCCTAGTACTCACGGGTTG | 212 | 51 |
| MDM4 | chr1 | 8 | 204511911 | 204512072 | 204511725 | 204512265 | 541 | TGAAGTCTAAACAAGGGAGG | 60 | AACTGAAGTTGGGCATTTAG | 213 | 52 |
| MDM4 | chr1 | 9 | 204513662 | 204513812 | 204513529 | 204514082 | 554 | GTCCACTGAATAAAGCCAAG | 61 | TACCTTGTTAGCAAAGGGAG | 214 | 53 |
| MDM4 | chr1 | 10 | 204515924 | 204516005 | 204515663 | 204516246 | 584 | TATGGGCATCTTCCTCTCTTC | 62 | CAGAGGCATTTATCTCATCC | 215 | 54 |
| MDM4 | chr1 | 11 | 204518240 | 204527248 | 204518078 | 204518653 | 576 | AAAGACTTTCCTTCATGTGG | 63 | AAGCTACACATGCTTCAAGAG | 216 | 55 |
| MDM4 | chr1 | 11 | 204518240 | 204527248 | 204518561 | 204519094 | 534 | AAGCATGGGAGAACAGTTAG | 64 | AAATGTCATGGAAGAAATC | 217 | 56 |
| MDM4 | chr1 | 11 | 204518240 | 204527248 | 204519011 | 204519570 | 560 | TACTTTATGCAGCAGTCAGG | 65 | CTATAATCCCAGCAATTTGG | 218 | 57 |
| MDM4 | chr1 | 11 | 204518240 | 204527248 | 204519551 | 204520101 | 551 | CCAAATTGCTGGGATTATAG | 66 | AAGACATGTTCTGACGGAAG | 219 | 58 |
| MDM4 | chr1 | 11 | 204518240 | 204527248 | 204519982 | 204520495 | 514 | CCCTGGGACTATAGATTTAGC | 67 | ATGACTCCTAAGACGCAAAG | 220 | 59 |
| MDM4 | chr1 | 11 | 204518240 | 204527248 | 204520474 | 204521069 | 596 | CTCTTTGCGTCTTAGGAGTC | 68 | GTGGTCAAGACAATTCTTC | 221 | 60 |
| MDM4 | chr1 | 11 | 204518240 | 204527248 | 204520897 | 204521454 | 558 | TGCAGAGACTGATCTTTGAG | 69 | ACCAACAACGACATTATGAG | 222 | 61 |
| MDM4 | chr1 | 11 | 204518240 | 204527248 | 204521434 | 204521966 | 533 | TCTCATAATGTCGTTGTTGG | 70 | GTAAAGATGAAATTCGGCTC | 223 | 62 |
| MDM4 | chr1 | 11 | 204518240 | 204527248 | 204521808 | 204522394 | 587 | TTGATCCTAAATTTGACACATC | 71 | GCCTTGCTTTAGTTTAGTGG | 224 | 63 |
| MDM4 | chr1 | 11 | 204518240 | 204527248 | 204522261 | 204522731 | 471 | AAAGTGCTGAGATTACAGGC | 72 | TGGTAATGTGGTGTGATTTC | 225 | 64 |
| MDM4 | chr1 | 11 | 204518240 | 204527248 | 204522686 | 204523254 | 596 | GCAACGTGCTGTAGACTATG | 73 | ATTGCATTGAATTGACACAC | 226 | 65 |
| MDM4 | chr1 | 11 | 204518240 | 204527248 | 204523103 | 204523650 | 548 | CAAGCATTTGAAATATGCAG | 74 | TCACGTTTGGTACATGAGAC | 227 | 66 |
| MDM4 | chr1 | 11 | 204518240 | 204527248 | 204523496 | 204524044 | 549 | TTAGTTCTGATGGTTCTCCC | 75 | TGCTGTATTCACCAATAACG | 228 | 67 |
| MDM4 | chr1 | 11 | 204518240 | 204527248 | 204523931 | 204524513 | 583 | TATAGGAGCCATTGGATTTC | 76 | GTCAGGAGATCAAGACCATC | 229 | 68 |

TABLE 2-continued

Exemplary selected regions of human genome for amplification or capture enrichment.

| Gene | Chr | Exon | Exon Start | Exon End | Primer Start | Primer End | Len | Fwd Primer | SEQ ID NO: | Rev Primer | SEQ ID NO: | SEQ ID NO: |
|---|---|---|---|---|---|---|---|---|---|---|---|---|
| MDM4 | chr1 | 11 | 204518240 | 204527248 | 204524182 | 204524677 | 496 | ATCTGAAATCCAAGATGCTG | 77 | TACAGCAACTGCTCTGAAAG | 230 | 69 |
| MDM4 | chr1 | 11 | 204518240 | 204527248 | 204524537 | 204525135 | 599 | TCCCAAAGTACTGGGATTAC | 78 | ATTTGCTACTGTTGACAGGG | 231 | 70 |
| MDM4 | chr1 | 11 | 204518240 | 204527248 | 204525034 | 204525491 | 458 | ATTTCTTATCTGAAGGCACTG | 79 | CATCACACACAGAAAGGAAG | 232 | 71 |
| MDM4 | chr1 | 11 | 204518240 | 204527248 | 204525312 | 204525853 | 542 | TACCAAAGACCCTTATCAGC | 80 | TTCTGTAAGAAGGAAGCCTG | 233 | 72 |
| MDM4 | chr1 | 11 | 204518240 | 204527248 | 204525814 | 204526369 | 556 | TGTCTCAAAGAAATTGAGGTC | 81 | AGTAATCAAACAGGCTCTGC | 234 | 73 |
| MDM4 | chr1 | 11 | 204518240 | 204527248 | 204526066 | 204526663 | 598 | TAAGTGCCTCTTGGGTAGAG | 82 | AGCTACTTGAGAGGTTGAGG | 235 | 74 |
| MDM4 | chr1 | 11 | 204518240 | 204527248 | 204526557 | 204527101 | 545 | GTCTTACTCTGTCACCCAGG | 83 | CTTTCCTCATCTAGTGAGCTG | 236 | 75 |
| MDM4 | chr1 | 11 | 204518240 | 204527248 | 204526920 | 204527482 | 563 | TCAGAGAATACACAGAGCAG | 84 | GATGGATTTCTTCAGGATTG | 237 | 76 |
| MYC | chr8 | 1 | 128748314 | 128748869 | 128748285 | 128748719 | 435 | CTTTATAATGCGAGGGTCTG | 85 | TTGTAAGTTCCAGTGCAAAG | 238 | 77 |
| MYC | chr8 | 1 | 128748314 | 128748869 | 128748485 | 128748945 | 461 | GTAGTAATTCAGCAGGAGG | 86 | ATTTAGGCATTGACTCATC | 239 | 78 |
| MYC | chr8 | 2 | 128750493 | 128751265 | 128750452 | 128750908 | 457 | TTTAACTCAAGACTGCCTCC | 87 | TACAGTCCTGGATGATGATG | 240 | 79 |
| MYC | chr8 | 2 | 128750493 | 128751265 | 128750834 | 128751381 | 548 | ACATGTGAACCAGAGTTTC | 88 | TCCAGATCGTCTATCTCTCC | 241 | 80 |
| MYC | chr8 | 3 | 128752641 | 128753680 | 128752528 | 128752893 | 366 | GTCCAGAGACCTTTCTAACG | 89 | TGATCTGTCTCAGGACTCTG | 242 | 88 |
| MYC | chr8 | 3 | 128752641 | 128753680 | 128752715 | 128753285 | 571 | AGAGTCTGGATCACCTTCTG | 90 | TTTTGATCATGCATTTGAAAC | 243 | 86 |
| MYC | chr8 | 3 | 128752641 | 128753680 | 128753173 | 128753687 | 515 | AACTTGAACACAGCTACGGAAC | 91 | TCACAACTTAAGATTTGGCTC | 244 | 87 |
| MYCL | chr1 | 1 | 40367479 | 40367687 | 40367327 | 40367715 | 389 | AGCGAGTTCAAAGCAAACTT | 92 | GCGACGAGATATAAGGCAGT | 245 | 81 |
| MYCL | chr1 | 2 | 40366610 | 40367115 | 40366514 | 40367080 | 567 | AGAGCTTGAGAGAGCCAAT | 93 | TTTCTACGACTATGACTGCG | 246 | 82 |
| MYCL | chr1 | 2 | 40366610 | 40367115 | 40367010 | 40367346 | 337 | ATTTCTTCCAGATGTCCTCG | 94 | AAGTTTGCTTTGAACTGCT | 247 | 83 |
| MYCL | chr1 | 3 | 40361095 | 40363642 | 40360973 | 40361525 | 553 | GAGTGGAATGACCAGGTTAG | 95 | ATGGTTTCTTTCTGAGGTTG | 248 | 84 |
| MYCL | chr1 | 3 | 40361095 | 40363642 | 40361453 | 40362039 | 587 | AGGGTAGAGAGGCTATTTCC | 96 | TTTTGAAGTTCTTCTGGAACC | 249 | 85 |
| MYCL | chr1 | 3 | 40361095 | 40363642 | 40362026 | 40362521 | 496 | AGAAGAACTTCAAACTTGCC | 97 | CATTGACCATTACCTCACTG | 250 | 89 |
| MYCL | chr1 | 3 | 40361095 | 40363642 | 40362463 | 40362896 | 434 | TAAAGGTTTCCAACTCCTTG | 98 | AATAAAGGCTTGCATTCTTG | 251 | 90 |
| MYCL | chr1 | 3 | 40361095 | 40363642 | 40363271 | 40363855 | 585 | CCAGGAAGTTGTGATTCTTC | 99 | TTTCCTTCTTGCTAATGTCC | 252 | 91 |

TABLE 2-continued

Exemplary selected regions of human genome for amplification or capture enrichment.

| Gene | Chr | Exon | Exon Start | Exon End | Primer Start | Primer End | Len | Fwd Primer | SEQ ID NO: | Rev Primer | SEQ ID NO: | ID |
|---|---|---|---|---|---|---|---|---|---|---|---|---|
| MYCN | chr2 | 1 | 16080559 | 16081175 | 16080527 | 16081017 | 491 | TTTTTATGGAAATCAGGAGG | 100 | ACCCAGAGATGGTTTTGTTT | 253 | 92 |
| MYCN | chr2 | 1 | 16080559 | 16081175 | 16080642 | 16081165 | 524 | GTTAATAATATCCCCGAGC | 101 | ACAGCTCAAACACAGACAGA | 254 | 93 |
| MYCN | chr2 | 1 | 16080559 | 16081175 | 16081147 | 16081538 | 392 | CTGTCTGTGTTTGAGCTGTC | 102 | AACAACAGACACCCATATCC | 255 | 94 |
| MYCN | chr2 | 2 | 16082069 | 16082976 | 16081882 | 16082346 | 465 | AGCTTGTACACAAAAGGAGG | 103 | CAAACTTCTTCCAGATGTCC | 256 | 95 |
| MYCN | chr2 | 2 | 16082069 | 16082976 | 16082241 | 16082780 | 540 | CTCGAGTTGACTCGCTACA | 104 | GTTCACGGGAAAGGGAAGA | 257 | 96 |
| MYCN | chr2 | 2 | 16082069 | 16082976 | 16082425 | 16082985 | 561 | AGATGCTGCTTGAGAACGAG | 105 | GGTCTTTACCTGAATCGCTC | 258 | 97 |
| MYCN | chr2 | 3 | 16085614 | 16087129 | 16085471 | 16086069 | 599 | ACATCTATGTTGATGGACCC | 106 | CTCATTCTTTACCAACTCCG | 259 | 98 |
| MYCN | chr2 | 3 | 16085614 | 16087129 | 16086055 | 16086635 | 581 | TTGGTAAAGAATGAGAAGGC | 107 | TGTCAATGGTATTACAGAAATG | 260 | 99 |
| MYCN | chr2 | 3 | 16085614 | 16087129 | 16086508 | 16087031 | 524 | GTTCCAAGTTTCCAAACAAC | 108 | AGAACTTTGCATTTACCCAG | 261 | 100 |
| MYCN | chr2 | 3 | 16085614 | 16087129 | 16087008 | 16087449 | 442 | AGAACTGGGTAAATGCAAAG | 109 | TGAGGTCTCAGTTAATTCC | 262 | 101 |
| NCOA3 | chr20 | 1 | 46130600 | 46130763 | 46130398 | 46130992 | 595 | AAAAATTAAGGGCAGGCTA | 110 | AGCTTCGTCTCAGCTCCTAC | 263 | 102 |
| NCOA3 | chr20 | 2 | 46211926 | 46212005 | 46211894 | 46212483 | 590 | AAATTCAATCCCTCTCTTC | 111 | AGGTGATCTAACACCTCAG | 264 | 103 |
| NCOA3 | chr20 | 3 | 46250972 | 46251074 | 46250747 | 46251198 | 452 | GGAACATTTCTGTCTTGGAG | 112 | ACTTACCACGAAGTGAAACC | 265 | 104 |
| NCOA3 | chr20 | 4 | 46252654 | 46252827 | 46252552 | 46253120 | 569 | GTAATCATGTAATAGTTGTTG TATAGGG | 113 | GATCTGTCACAGTTTCTCCC | 266 | 105 |
| NCOA3 | chr20 | 5 | 46254124 | 46254225 | 46253918 | 46254512 | 595 | TTAGTTATCTTCTGGCTTCC | 114 | TACAGGCTACCTTTCCTTTC | 267 | 106 |
| NCOA3 | chr20 | 6 | 46255745 | 46255920 | 46255621 | 46256183 | 563 | TTACCTCCTTGGAAGGTCTTG | 115 | ATTTCAGGCTGGCAATATAC | 268 | 107 |
| NCOA3 | chr20 | 7 | 46256304 | 46256493 | 46256232 | 46256752 | 521 | CTTGAATTCTTGATGATGGTC | 116 | TGGTAATAAAGCTCTCAGGG | 269 | 108 |
| NCOA3 | chr20 | 8 | 46256665 | 46256767 | 46256391 | 46256976 | 586 | ATTCTGGAAGACATAAACGC | 117 | AACATACCCAATTCAAATGC | 270 | 109 |
| NCOA3 | chr20 | 9 | 46262239 | 46262380 | 46262160 | 46262475 | 316 | CAGTGCTAAGCCATGTGTAG | 118 | TAAATCCAGGAGTTCGAGTC | 271 | 110 |
| NCOA3 | chr20 | 10 | 46262791 | 46262939 | 46262711 | 46263063 | 353 | GTATATTTCCTCCCTGTCCC | 119 | CATCAAACCCATAACCTTC | 272 | 111 |
| NCOA3 | chr20 | 11 | 46264065 | 46264457 | 46263932 | 46264470 | 539 | CAAAGTGCTGGGAATATAGG | 120 | TCAACACAAATACCTGCAAC | 273 | 112 |
| NCOA3 | chr20 | 12 | 46264634 | 46265506 | 46264235 | 46264834 | 600 | ATGAGTGGAGCTAGGTATGG | 121 | CTTGGAATCCTGATTGCTTA | 274 | 113 |
| NCOA3 | chr20 | 12 | 46264634 | 46265506 | 46264800 | 46265238 | 439 | CCCAACCAAGTAAAGTAAGC | 122 | GCAGTATATCTTGCTACCTC | 275 | 114 |

TABLE 2-continued

Exemplary selected regions of human genome for amplification or capture enrichment.

| Gene | Chr | Exon | Exon Start | Exon End | Primer Start | Primer End | Len | Fwd Primer | SEQ ID NO: | Rev Primer | SEQ ID NO: |
|---|---|---|---|---|---|---|---|---|---|---|---|
| NCOA3 | chr20 | 12 | 46264634 | 46265506 | 46265206 | 46265783 | 578 | GAATTCACCAGCTGAGGTAG | 123 | CTCTTAATGACCCAATCTGC | 276 | 115 |
| NCOA3 | chr20 | 13 | 46266391 | 46266527 | 46266333 | 46266855 | 523 | TGTTTATACCTGTGTGTCTGG | 124 | TTAATCCAGTTCTCTGTGGC | 277 | 116 |
| NCOA3 | chr20 | 14 | 46267751 | 46267946 | 46267493 | 46268028 | 536 | AGTTCTCAGTACTTCAGCCG | 125 | CTCCCAATTATTAGATGGC | 278 | 117 |
| NCOA3 | chr20 | 15 | 46268320 | 46268566 | 46268163 | 46268576 | 414 | ATAGTGGCCTATGTCTCCAC | 126 | GGACACTTACTCATTTGAAGC | 279 | 118 |
| NCOA3 | chr20 | 16 | 46268668 | 46268795 | 46268503 | 46268943 | 441 | CGGTCTAATAGCATACCAGG | 127 | AGAGTTACACAGAGAAATGCC | 280 | 119 |
| NCOA3 | chr20 | 17 | 46270956 | 46271128 | 46270628 | 46271179 | 552 | AGGAGTATCTTCTCCCATCC | 128 | GCGCACACACACAAATATAC | 281 | 120 |
| NCOA3 | chr20 | 18 | 46275816 | 46276110 | 46275557 | 46276087 | 531 | CACAGTACACCTGGTTCTTG | 129 | GAAGCTGCATTCTAAGTTGC | 282 | 121 |
| NCOA3 | chr20 | 18 | 46275816 | 46276110 | 46275868 | 46276458 | 591 | GTAATGATGGATCAGAGAGGC | 130 | AAATGCTGAAATCAAGAAGG | 283 | 122 |
| NCOA3 | chr20 | 19 | 46277748 | 46277853 | 46277654 | 46278204 | 551 | GATATTACCTCATTGGCTGG | 131 | TGCATGTTGTTTCATAATCC | 284 | 123 |
| NCOA3 | chr20 | 20 | 46279728 | 46280020 | 46279700 | 46280285 | 586 | TAATTGCCACTCTTTCTTGGG | 132 | AACTTTGCAGTGTTCTTCC | 285 | 124 |
| NCOA3 | chr20 | 21 | 46281149 | 46281324 | 46281096 | 46281383 | 288 | TTCTAAGGAGAAGGCATTTG | 133 | TAAGTTCTTGGACTTCTGGG | 286 | 125 |
| NCOA3 | chr20 | 22 | 46281674 | 46281816 | 46281629 | 46282021 | 393 | GCTAAAGTGGACTTCCAGAGG | 134 | GAGATCCCATCTTACACATGC | 287 | 126 |
| NCOA3 | chr20 | 23 | 46282149 | 46285621 | 46282008 | 46282592 | 585 | TAAGATGGGATCTCAGGAAC | 135 | TCTTTGTCCAATACTGCAAC | 288 | 127 |
| NCOA3 | chr20 | 23 | 46282149 | 46285621 | 46282430 | 46282949 | 520 | ATTCTGGAGACATGGAGTGT | 136 | AACCAGGAATGTGTTTCACT | 289 | 128 |
| NCOA3 | chr20 | 23 | 46282149 | 46285621 | 46282912 | 46283260 | 349 | TTGAGGTCTTGAGGGAATAG | 137 | ACCACACAGCTTACTGAAATC | 290 | 129 |
| NCOA3 | chr20 | 23 | 46282149 | 46285621 | 46283242 | 46283793 | 552 | TTTCAGTAAGCTGTGTGGTG | 138 | AGGGACATAATGAAAGCATC | 291 | 230 |
| NCOA3 | chr20 | 23 | 46282149 | 46285621 | 46283688 | 46284229 | 542 | GACCTGAATCCCATATTGAG | 139 | GTGGGTCTGGAAATAATCAG | 292 | 131 |
| NCOA3 | chr20 | 23 | 46282149 | 46285621 | 46284210 | 46284671 | 462 | CTGATTATTTCCAGACCCAC | 140 | AGAAATCTTGAGTTTGCACC | 293 | 139 |
| NCOA3 | chr20 | 23 | 46282149 | 46285621 | 46284324 | 46284768 | 445 | AAATCCGAAAACTTCCATTG | 141 | GAGGAGAGGTAGACAGCAGG | 294 | 137 |
| NCOA3 | chr20 | 23 | 46282149 | 46285621 | 46284746 | 46285291 | 546 | ACTCCTGCTGTCTACCTCTC | 142 | TGCTCCTAGGAACCTAATTG | 295 | 138 |
| NCOA3 | chr20 | 23 | 46282149 | 46285621 | 46285161 | 46285693 | 533 | AGTTCTTTGATCCAGAGGTG | 143 | TTCCTTAACCTCCTTTACCC | 296 | 132 |
| NKX2-1 | chr14 | 1 | 36989257 | 36989430 | 36989105 | 36989609 | 505 | AGGAGAGATGGTTGAGAGGA | 144 | ACTGAAAAACCCCTGAGCTG | 297 | 133 |
| NKX2-1 | chr14 | 2 | 36988189 | 36988575 | 36987990 | 36988496 | 507 | GCTACCAAGTGCCTGTTCTT | 145 | AGCTACAAGAAAGTGGGCAT | 298 | 134 |

TABLE 2-continued

Exemplary selected regions of human genome for amplification or capture enrichment.

| Gene | Chr | Exon | Exon Start | Exon End | Primer Start | Primer End | Len | Fwd Primer | SEQ ID NO: | Rev Primer | SEQ ID NO: |
|---|---|---|---|---|---|---|---|---|---|---|---|
| NKX2-1 | chr14 | 2 | 36988189 | 36988575 | 36988249 | 36988667 | 422 | TTCCCTCATGGTGTCCTGGTA | 146 | ACCAGAATATTTGGCAAAGG | 299 | 135 |
| NKX2-1 | chr14 | 3 | 36985603 | 36987225 | 36985377 | 36985969 | 593 | ACTGCTCAAGATTTGTTTCC | 147 | TCACTGACACAAAGGAAGTG | 300 | 136 |
| NKX2-1 | chr14 | 3 | 36985603 | 36987225 | 36985737 | 36986227 | 491 | TACACAGATTTGTCAATGCC | 148 | ATCTTTAAGCAGAGAAGGGC | 301 | 140 |
| NKX2-1 | chr14 | 3 | 36985603 | 36987225 | 36986160 | 36986513 | 354 | GAAAACCCATTTGAATCACC | 149 | CTCCACCTTGCTATACGGTC | 302 | 141 |
| NKX2-1 | chr14 | 3 | 36985603 | 36987225 | 36986374 | 36986970 | 597 | TGTTAAGAAAAGTCGAAGCG | 150 | AGAACCACCGCTACAAAATG | 303 | 142 |
| NKX2-1 | chr14 | 3 | 36985603 | 36987225 | 36986967 | 36987556 | 590 | TTCTGAACCAGATCTTGAC | 151 | TAATCCTAATGCTCTGACCC | 304 | 143 |
| SKP2 | chr5 | 1 | 36152144 | 36152372 | 36152137 | 36152620 | 484 | GAAACTACAATTCCCAGCAG | 152 | GAGAGACCAGGGCAATCATAC | 305 | 144 |
| SKP2 | chr5 | 2 | 36152872 | 36153144 | 36152615 | 36153148 | 534 | TCTCTCTCCTTGTCTGTTCC | 153 | TTACCTGGAAAGTTCTCTCG | 306 | 145 |
| SKP2 | chr5 | 3 | 36163746 | 36163858 | 36163699 | 36164087 | 389 | GATAGGGTGAAAGAATGGTG | 154 | ACTGAATACAGGGCAAAGAG | 307 | 146 |
| SKP2 | chr5 | 4 | 36166620 | 36166764 | 36166512 | 36167017 | 504 | GCTTCAAGGAGGATTAGCAG | 155 | AAGACAAATGTGCCTCTTTC | 308 | 147 |
| SKP2 | chr5 | 5 | 36168414 | 36168549 | 36168352 | 36168852 | 501 | GTTTGAAATTGGATGTACCC | 156 | CAGCATTCACTAACAAGGTG | 309 | 148 |
| SKP2 | chr5 | 6 | 36170445 | 36170544 | 36170281 | 36170703 | 423 | GAGGCAAATTATCCTGTTTG | 157 | TTGGACAGAAAGTTAGGAGG | 310 | 149 |
| SKP2 | chr5 | 7 | 36171704 | 36171835 | 36171414 | 36171948 | 535 | AAGACTGGCATTTCTACCTG | 158 | CATGCACTGGATTAAATGAG | 311 | 150 |
| SKP2 | chr5 | 8 | 36177066 | 36177118 | 36176945 | 36177324 | 380 | GTGTGGTTCTAATTGCATTG | 159 | ATTCCTGAAAGCAGTCATTC | 312 | 151 |
| SKP2 | chr5 | 9 | 36177286 | 36177394 | 36177180 | 36177543 | 364 | GGGAAAGGATCATAATGTTG | 160 | CTCTGCTGGTCTTTCATAGC | 313 | 152 |
| SKP2 | chr5 | 10 | 36183941 | 36184142 | 36183823 | 36184304 | 482 | TGCCTTTATCTGCTTAGACC | 161 | CAAGCATATGAAGTAGATGGG | 314 | 153 |

In some cases, amplification primers designed to amplify a portion of a human genome targeted by one or more of the FISH probes (e.g., a FISH probe set forth in Table 3) can be used in a single assay as described herein. For example, amplification primers designed to amplify a portion of a human genome targeted by 5, 10, 20, or more FISH probes can be used in a single assay as described herein. In some cases, two or more different amplification primer pairs can be designed to amplify different portions of the same region of a human genome targeted by one of a FISH probe. For example, three primer pairs can be designed to amplify three different regions of the first FISH probe listed in Table 3. In some cases, as described herein, nucleic acid capture techniques can be used in addition to or in place of amplification techniques to increase sequence read coverage.

The invention will be further described in the following examples, which do not limit the scope of the invention described in the claims.

EXAMPLES

Example 1—Combining LC-WGS and Targeted Nucleic Acid Amplification to Improve the Interpretation of Cancer Panel Tests The combination of LC-WGS and targeted nucleic acid amplification is used to improve the clinical interpretation of Cancer Panel Tests that focus primarily on identifying mutations driving tumorgenesis in targeted regions of the genome. LC-WGS provides information in the genome wide nature and location of amplifications and deletions. This information is used to assess the aggressiveness of the tumor and/or provide additional support to the mutations reported in the targeted regions.

Figure 4A:
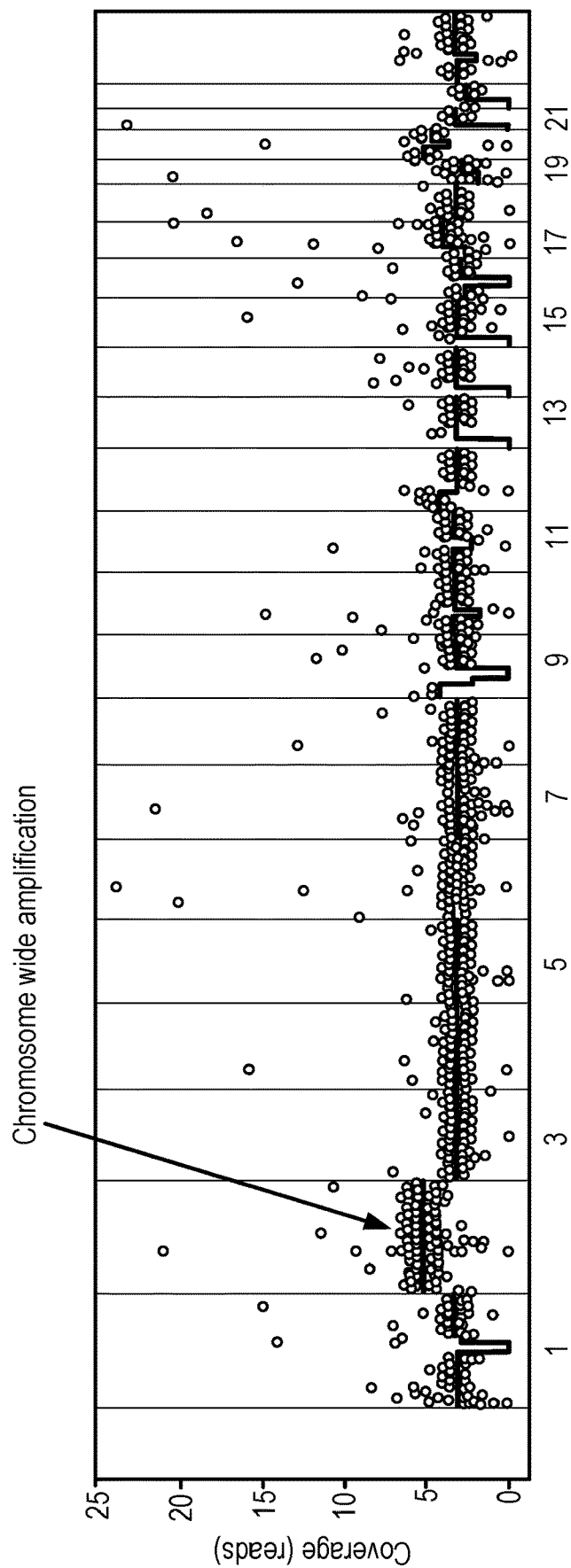
FIGS. 4A and 4B. LC-WGS coverage computed from the reads extracted from a targeted amplification assay where PCR amplification was performed below saturation. No-coverage regions correspond to centromers. Chromosome wide amplification, local and complex patterns of amplification are clearly visible in these plots.
Figure 4B:
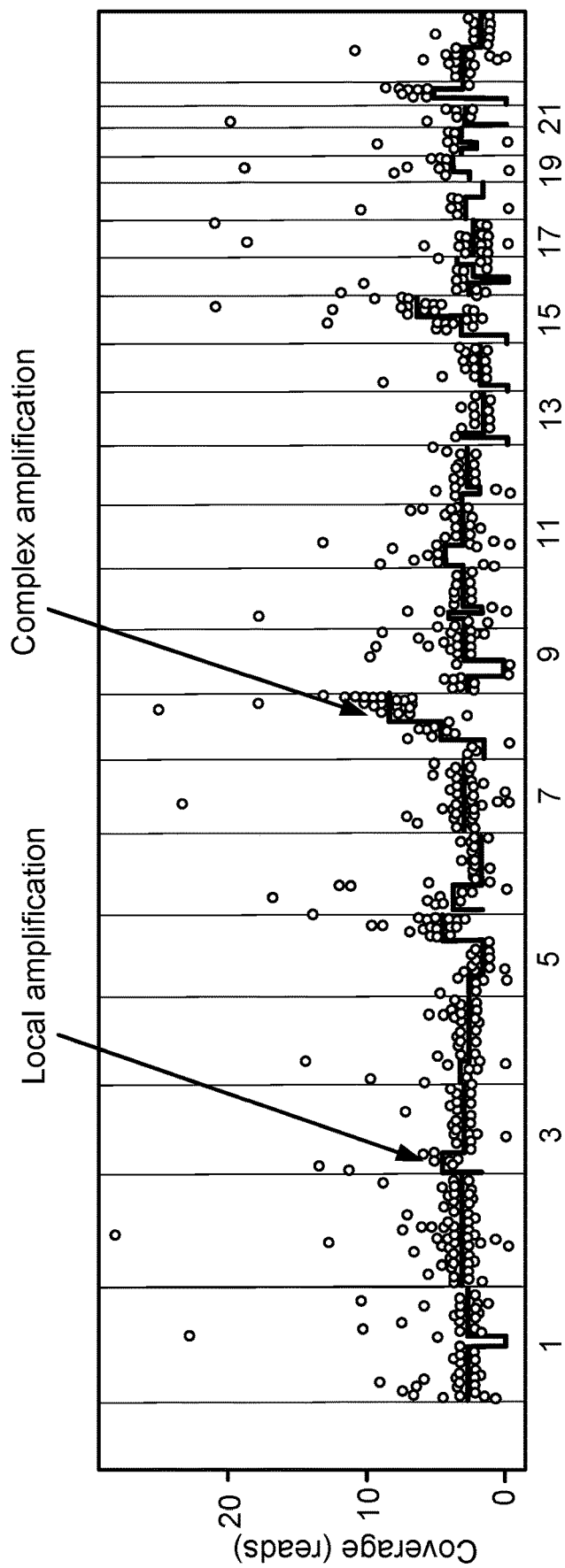

The values of combining LC-WGS and targeted nucleic acid amplification was highlighted by performing the following. Whole DNA of biospecimens was extracted. Targeted regions amplification was performed using an amplicon-based protocol to allow variant calling. The targeted amplification was performed using a number of cycles that was protocol specific, but might vary from protocol to protocol (15 to 20 cycles). The amplification was done below saturation level, leaving in solution about 25% of reads that do not map to the target regions but map the remaining areas of the genome. Upon sequencing, 3.5M reads in total were obtained. The 2.6M reads mapping the target regions were extracted and processed for variant calling using a DNA processing workflow. The high coverage of these regions (at about 1000× average coverage) allowed for clinical grade variants calling. For the two ovarian samples displayed on FIGS. 4A and 4B, mutations in the DNA repair and signal transduction genes were reported in the clinical report.

The 0.9M remaining reads (not mapped to these targeted regions) were processed. The resulting aligned reads were clustered in 10 kb bins. The count of the reads in each bin was displayed on FIGS. 4A and 4B for two ovarian tumor samples. The plots clearly highlighted chromosome level amplifications and target local amplifications that can be used to further refine the interpretation of the mutations. For example, the balance of chromosome or chromosome arm amplification and local amplification can be informative of the aggressiveness of the tumor.

Example 2—Combining LC-WGS and Targeted Nucleic Acid Amplification to Replace a FISH Assay FISH assays are commonly used by clinical laboratories to report the presence of cancer cells in cytology specimens. For example, the UroVysion FISH assay (Abbott Molecular Inc.) is used to identify cancer cells in urine and biliary samples. This FISH assay includes a set of four fluorescent probes that target the chromosomal location 9p21 and the centromeres of chromosomes 3, 7, and 17. Probes targeting chromosomal locations are used to report amplifications and deletions in these regions. The ones targeting centromeres identify the loss or the presence of additional copies of chromosomes.

For lung and pleural samples, the LaVysion FISH assay (Abbott Molecular Inc.) is used. The four fluorescent probes of this assay target chromosomal locations 7p12, 5p12, 8q24, and the centromere of chromosome 6. Each of these FISH probes is greater than 150,000 bases. The probes are of large size to ensure that their luminescence is high enough to be observed under a microscope.

An assay is designed as described herein to identify deletions and/or amplifications in the genomic regions targeted by the FISH probes, while also having the ability to provide a low resolution global view of alterations across the genome. The regions amplified by these primers overlap with the ones targeted by the FISH probes. The amplified regions are not the same size as the FISH probes since the FISH probes are often greater than 150,000 bases long for technical reasons that are specific to the FISH assay. The FISH probes that target centromeres identify whole chromosome amplifications and/or deletions, which will be identified by the LC-WGS of the designed assay.

In particular, the designed assay combines both the UroVysion and LaVysion in a single assay as set forth in Table 3. Table 3 provides a list of primers that are used to amplify genomic regions 9p21, 7p12, 5p12, and 8q24. The design of these primers was optimized for a melting temperature of about 60 degrees. Primers for the FISH probes targeting centromere regions were not included since the LC-WGS component of the designed assay can identify genomic amplifications and/or deletions of whole chromosomes. Table 3 provides in the 1st column the cytoband location of the regions amplified by the primers followed by the genomic start and end coordinates of the region amplified by the primers, the length of the amplified genomic region, and the sequence of the forward and reverse primers.

TABLE 3

Example of the design of an assay that replaces two FISH assays.

| Cytoband | start | end | length | forward | reverse |
| --- | --- | --- | --- | --- | --- |
| 9p21 | 26549942 | 26550536 | 595 | GTCTGGTTCTGGCT CTGTGC (SEQ ID NO: 1) | GCCACCTCCTCTTT GTCAGC (SEQ ID NO: 2) |

TABLE 3-continued

Example of the design of
an assay that replaces two FISH assays.

| Cytoband | start | end | length | forward | reverse |
|---|---|---|---|---|---|
| 7p12 | 51867623 | 51868189 | 567 | AAGAGTTGCCAAGG CACGAC (SEQ ID NO: 3) | TGACAGGCTTGAAT GCACCC (SEQ ID NO: 4) |
| 5p12 | 43864904 | 43865490 | 587 | AGACTTCACCTTTG GTGCCC (SEQ ID NO: 5) | CCTGGAGAACAGGA TGCGAC (SEQ ID NO: 6) |
| 8q24 | 130915820 | 130916382 | 563 | TTCAACCAACCCAT CAGCGG (SEQ ID NO: 7) | TTCATGGCCACCAC AATGGC (SEQ ID NO: 8) |

Example 3—Single Assay for the Combined Reporting for Fetal Fraction Estimation and the Presence to Fetal Trisomy from the Blood of the Mother LC-WGS sequencing has been successfully applied to the detection fetal trisomy from the blood of pregnant women. However, to optimize the selectivity and sensitivity of LC-WGS, an additional test is needed to measure the fetal fraction. This additional test can be implemented using SNP microarrays to measure the allelic imbalance. Some in silico approaches (e.g., bioinformatics) also have been used for the same purpose.

An assay is designed as described herein to identify in a single assay both the fetal fraction in the blood of the mother and the presence of fetal trisomy. For this assay, the amplified regions are designed to target SNPs empirically selected to maximize the likelihood to be heterogeneous in the fetus and homozygous in the mother. The ratio of the reads mapped to the major and minor allele is informative of the fraction of the DNA from the fetus present in the blood of the mother. Calling the genotypes of SNPs is not possible from LC-WGS alone since this technique does not have enough reads available to call genotypes.

Example 4—Combining LC-WGS and Targeted Nucleic Acid Amplification for the Early Detection of Cancer The methods and materials provided herein are used for the early detection of cancer in cell free DNA. As tumors develop, a significant percentage of tumor cells die, shedding their abnormal DNA in the blood stream. The methods and materials provided herein are used to detect genomic amplification and/or deletion events in cell free DNA, thereby detecting the presence of a tumor. The low coverage whole genome sequencing of the assay provides a low resolution whole genome view of amplifications and/or deletions, while oncogenes frequently observed as being amplified and/or deleted across cancers are assessed at a higher sensitivity level using PCR amplification targeted regions. The following genes, which are frequently amplified across tumor types, are enriched as described herein: CCND1, LMO1, MDM2, MDM4, MYC, MYCL1, MYCN, NCOA3, NKX2-1, and SKP2. With the designed assay, multiple amplicons (e.g., about 5) of about 150 bp in length are assessed for each gene (for a total of about 50 amplicons per assay). Assuming that 400,000 reads of 150 bp is sequenced per sample, if 50 amplicons of 150 bp are used to amplify 50 regions of the genome, then each region exhibits a coverage of about 600× while the LC-WGS maintains an average coverage of about 1× for the DNA not enriched (Table 4).

TABLE 4

| reads per sample | read length (bp) | number of amplified regions | length of amplified regions | coverage of the amplified regions | LC-WGS coverage |
|---|---|---|---|---|---|
| 30,000,000 | 150 | 50 | 150 | 600× | 1.0 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing the number of sequencing reads of one or more pre-selected genomic regions using low coverage whole genome sequencing, wherein said method comprises performing an amplification reaction using a genomic nucleic acid sample to amplify one or more pre-selected genomic regions, thereby forming an amplified sample, and performing low coverage whole genome sequencing using said amplified sample, wherein the coverage of said pre-selected genomic regions using said low coverage whole genome sequencing is greater than 250×, and wherein the coverage of regions outside said pre-selected genomic regions using said low coverage whole genome sequencing is less than 10×.

2. The method of claim 1, wherein said one or more pre-selected genomic regions is from one pre-selected genomic region to 2500 pre-selected genomic regions.

3. The method of claim 1, wherein said one or more pre-selected genomic regions is from one pre-selected genomic region to 2000 pre-selected genomic regions.

4. The method of claim 1, wherein said one or more pre-selected genomic regions is from one pre-selected genomic region to 1500 pre-selected genomic regions.

5. The method of claim 1, wherein said low coverage whole genome sequencing is whole genome sequencing with less than 2× genome wide coverage.

6. The method of claim 1, wherein said low coverage whole genome sequencing is whole genome sequencing with less than 1× genome wide coverage.

7. The method of claim 1, wherein said genomic nucleic acid sample is a human genomic nucleic acid sample.

8. The method of claim 1, wherein the coverage of said pre-selected genomic regions using said low coverage whole genome sequencing is greater than 500×.

9. The method of claim 1, wherein the coverage of said pre-selected genomic regions using said low coverage whole genome sequencing is greater than 1000×.

10. The method of claim 1, wherein said method comprises performing said amplification reaction using said genomic nucleic acid sample to amplify one or more pre-selected genomic regions having a length from about 150 bp to about 750 bp.

11. The method of claim 1, wherein said low coverage whole genome sequencing is whole genome sequencing with less than 5× genome wide coverage.

12. The method of claim 1, wherein said low coverage whole genome sequencing is whole genome sequencing with less than 3× genome wide coverage.

* * * * *

SEQUENCE LISTING

<160> NUMBER OF SEQ ID NOS: 314

<210> SEQ ID NO 1
<211> LENGTH: 20
<212> TYPE: DNA
<213> ORGANISM: Homo sapiens

<400> SEQUENCE: 1
gtctggttct ggctctgtgc                    20

```
<210> SEQ ID NO 2
<211> LENGTH: 20
<212> TYPE: DNA
<213> ORGANISM: Homo sapiens

<400> SEQUENCE: 2
gccacctcct ctttgtcagc                                              20

<210> SEQ ID NO 3
<211> LENGTH: 20
<212> TYPE: DNA
<213> ORGANISM: Homo sapiens

<400> SEQUENCE: 3
aagagttgcc aaggcacgac                                              20

<210> SEQ ID NO 4
<211> LENGTH: 20
<212> TYPE: DNA
<213> ORGANISM: Homo sapiens

<400> SEQUENCE: 4
tgacaggctt gaatgcaccc                                              20

<210> SEQ ID NO 5
<211> LENGTH: 20
<212> TYPE: DNA
<213> ORGANISM: Homo sapiens

<400> SEQUENCE: 5
agacttcacc tttggtgccc                                              20

<210> SEQ ID NO 6
<211> LENGTH: 20
<212> TYPE: DNA
<213> ORGANISM: Homo sapiens

<400> SEQUENCE: 6
cctggagaac aggatgcgac                                              20

<210> SEQ ID NO 7
<211> LENGTH: 20
<212> TYPE: DNA
<213> ORGANISM: Homo sapiens

<400> SEQUENCE: 7
ttcaaccaac ccatcagcgg                                              20

<210> SEQ ID NO 8
<211> LENGTH: 20
<212> TYPE: DNA
<213> ORGANISM: Homo sapiens

<400> SEQUENCE: 8
ttcatggcca ccacaatggc                                              20

<210> SEQ ID NO 9
<211> LENGTH: 20
<212> TYPE: DNA
<213> ORGANISM: Homo sapiens

<400> SEQUENCE: 9
ggctttgatc tttgcttaac                                              20
```

```
<210> SEQ ID NO 10
<211> LENGTH: 20
<212> TYPE: DNA
<213> ORGANISM: Homo sapiens

<400> SEQUENCE: 10
ggactttccc tttcagtttc                                              20

<210> SEQ ID NO 11
<211> LENGTH: 20
<212> TYPE: DNA
<213> ORGANISM: Homo sapiens

<400> SEQUENCE: 11
ggaggtcttt ttgtttccac                                              20

<210> SEQ ID NO 12
<211> LENGTH: 21
<212> TYPE: DNA
<213> ORGANISM: Homo sapiens

<400> SEQUENCE: 12
ttccttggtt atgtttgagt c                                            21

<210> SEQ ID NO 13
<211> LENGTH: 20
<212> TYPE: DNA
<213> ORGANISM: Homo sapiens

<400> SEQUENCE: 13
ttgctcttat aaaggcttcc                                              20

<210> SEQ ID NO 14
<211> LENGTH: 20
<212> TYPE: DNA
<213> ORGANISM: Homo sapiens

<400> SEQUENCE: 14
aagcttcatt ctccttgttg                                              20

<210> SEQ ID NO 15
<211> LENGTH: 20
<212> TYPE: DNA
<213> ORGANISM: Homo sapiens

<400> SEQUENCE: 15
gcatctctgt actttgcttg                                              20

<210> SEQ ID NO 16
<211> LENGTH: 20
<212> TYPE: DNA
<213> ORGANISM: Homo sapiens

<400> SEQUENCE: 16
atttccaagc actttcagtc                                              20

<210> SEQ ID NO 17
<211> LENGTH: 20
<212> TYPE: DNA
<213> ORGANISM: Homo sapiens

<400> SEQUENCE: 17
```
acacacacac acaaaccttc                                                    20

<210> SEQ ID NO 18
<211> LENGTH: 20
<212> TYPE: DNA
<213> ORGANISM: Homo sapiens

<400> SEQUENCE: 18
ggaaatattc acatcgcttc                                                    20

<210> SEQ ID NO 19
<211> LENGTH: 20
<212> TYPE: DNA
<213> ORGANISM: Homo sapiens

<400> SEQUENCE: 19
tgtttcacaa tacctcatgc                                                    20

<210> SEQ ID NO 20
<211> LENGTH: 20
<212> TYPE: DNA
<213> ORGANISM: Homo sapiens

<400> SEQUENCE: 20
acctgtagga ctctcattcg                                                    20

<210> SEQ ID NO 21
<211> LENGTH: 20
<212> TYPE: DNA
<213> ORGANISM: Homo sapiens

<400> SEQUENCE: 21
tcctggatgt tgtgtgtatc                                                    20

<210> SEQ ID NO 22
<211> LENGTH: 20
<212> TYPE: DNA
<213> ORGANISM: Homo sapiens

<400> SEQUENCE: 22
gagacttcct aatcccgccg                                                    20

<210> SEQ ID NO 23
<211> LENGTH: 20
<212> TYPE: DNA
<213> ORGANISM: Homo sapiens

<400> SEQUENCE: 23
gagaggacac acagggtact                                                    20

<210> SEQ ID NO 24
<211> LENGTH: 20
<212> TYPE: DNA
<213> ORGANISM: Homo sapiens

<400> SEQUENCE: 24
tattcacaca gaaatgtgcc                                                    20

<210> SEQ ID NO 25
<211> LENGTH: 20
<212> TYPE: DNA
<213> ORGANISM: Homo sapiens

<400> SEQUENCE: 25

```
aggtctgtgt cagtcatgtg                                              20

<210> SEQ ID NO 26
<211> LENGTH: 20
<212> TYPE: DNA
<213> ORGANISM: Homo sapiens

<400> SEQUENCE: 26
ggctaaagga gtgtcacagc                                              20

<210> SEQ ID NO 27
<211> LENGTH: 20
<212> TYPE: DNA
<213> ORGANISM: Homo sapiens

<400> SEQUENCE: 27
aagtcctgac ttgtctccag                                              20

<210> SEQ ID NO 28
<211> LENGTH: 20
<212> TYPE: DNA
<213> ORGANISM: Homo sapiens

<400> SEQUENCE: 28
tggattggat actgtctgtg                                              20

<210> SEQ ID NO 29
<211> LENGTH: 20
<212> TYPE: DNA
<213> ORGANISM: Homo sapiens

<400> SEQUENCE: 29
ttagtagaga tgggaccagg                                              20

<210> SEQ ID NO 30
<211> LENGTH: 21
<212> TYPE: DNA
<213> ORGANISM: Homo sapiens

<400> SEQUENCE: 30
tttgaatgtg tgcagtagtt c                                            21

<210> SEQ ID NO 31
<211> LENGTH: 20
<212> TYPE: DNA
<213> ORGANISM: Homo sapiens

<400> SEQUENCE: 31
aaattgcata agggtttgtg                                              20

<210> SEQ ID NO 32
<211> LENGTH: 20
<212> TYPE: DNA
<213> ORGANISM: Homo sapiens

<400> SEQUENCE: 32
catctgtgag tgagaacagg                                              20

<210> SEQ ID NO 33
<211> LENGTH: 20
<212> TYPE: DNA
<213> ORGANISM: Homo sapiens
```

```
<400> SEQUENCE: 33
agattgtgcc tctgtactcc                                               20

<210> SEQ ID NO 34
<211> LENGTH: 20
<212> TYPE: DNA
<213> ORGANISM: Homo sapiens

<400> SEQUENCE: 34
acagaggtca agaggtgatg                                               20

<210> SEQ ID NO 35
<211> LENGTH: 20
<212> TYPE: DNA
<213> ORGANISM: Homo sapiens

<400> SEQUENCE: 35
tctgattgaa ggaaataggg                                               20

<210> SEQ ID NO 36
<211> LENGTH: 20
<212> TYPE: DNA
<213> ORGANISM: Homo sapiens

<400> SEQUENCE: 36
aaacactgaa tattgagccc                                               20

<210> SEQ ID NO 37
<211> LENGTH: 20
<212> TYPE: DNA
<213> ORGANISM: Homo sapiens

<400> SEQUENCE: 37
cagagagtca tgtgttgagg                                               20

<210> SEQ ID NO 38
<211> LENGTH: 20
<212> TYPE: DNA
<213> ORGANISM: Homo sapiens

<400> SEQUENCE: 38
agctcatcct ttacaccaac                                               20

<210> SEQ ID NO 39
<211> LENGTH: 20
<212> TYPE: DNA
<213> ORGANISM: Homo sapiens

<400> SEQUENCE: 39
gcagtgtcat gatctagcag                                               20

<210> SEQ ID NO 40
<211> LENGTH: 20
<212> TYPE: DNA
<213> ORGANISM: Homo sapiens

<400> SEQUENCE: 40
tctgggttca agctattctc                                               20

<210> SEQ ID NO 41
<211> LENGTH: 20
<212> TYPE: DNA
<213> ORGANISM: Homo sapiens
```

```
<400> SEQUENCE: 41
gctaagtagg attacaggcg                                              20

<210> SEQ ID NO 42
<211> LENGTH: 20
<212> TYPE: DNA
<213> ORGANISM: Homo sapiens

<400> SEQUENCE: 42
taaagtacct tcttggcctg                                              20

<210> SEQ ID NO 43
<211> LENGTH: 20
<212> TYPE: DNA
<213> ORGANISM: Homo sapiens

<400> SEQUENCE: 43
gtgttagttt ctttgggacc                                              20

<210> SEQ ID NO 44
<211> LENGTH: 21
<212> TYPE: DNA
<213> ORGANISM: Homo sapiens

<400> SEQUENCE: 44
ctcctttgga gacttagaac c                                            21

<210> SEQ ID NO 45
<211> LENGTH: 20
<212> TYPE: DNA
<213> ORGANISM: Homo sapiens

<400> SEQUENCE: 45
aagggaggat ataaggaacc                                              20

<210> SEQ ID NO 46
<211> LENGTH: 20
<212> TYPE: DNA
<213> ORGANISM: Homo sapiens

<400> SEQUENCE: 46
ccaaataatg ctttgaggac                                              20

<210> SEQ ID NO 47
<211> LENGTH: 20
<212> TYPE: DNA
<213> ORGANISM: Homo sapiens

<400> SEQUENCE: 47
ggactgaggt aattctgcac                                              20

<210> SEQ ID NO 48
<211> LENGTH: 20
<212> TYPE: DNA
<213> ORGANISM: Homo sapiens

<400> SEQUENCE: 48
agctacaacc aagcagaatc                                              20

<210> SEQ ID NO 49
<211> LENGTH: 20
<212> TYPE: DNA
```

```
<213> ORGANISM: Homo sapiens

<400> SEQUENCE: 49
ttctgaggag tatcggtagc                                          20

<210> SEQ ID NO 50
<211> LENGTH: 20
<212> TYPE: DNA
<213> ORGANISM: Homo sapiens

<400> SEQUENCE: 50
cttctcttag gtcacatggc                                          20

<210> SEQ ID NO 51
<211> LENGTH: 20
<212> TYPE: DNA
<213> ORGANISM: Homo sapiens

<400> SEQUENCE: 51
ttgtgaggca caaatgtaag                                          20

<210> SEQ ID NO 52
<211> LENGTH: 20
<212> TYPE: DNA
<213> ORGANISM: Homo sapiens

<400> SEQUENCE: 52
ggtctgtagg cttatgatgg                                          20

<210> SEQ ID NO 53
<211> LENGTH: 20
<212> TYPE: DNA
<213> ORGANISM: Homo sapiens

<400> SEQUENCE: 53
aaatctgacg actttcaacc                                          20

<210> SEQ ID NO 54
<211> LENGTH: 20
<212> TYPE: DNA
<213> ORGANISM: Homo sapiens

<400> SEQUENCE: 54
aagatatgca gaacctcagc                                          20

<210> SEQ ID NO 55
<211> LENGTH: 20
<212> TYPE: DNA
<213> ORGANISM: Homo sapiens

<400> SEQUENCE: 55
aaattacctg gatatggtgg                                          20

<210> SEQ ID NO 56
<211> LENGTH: 20
<212> TYPE: DNA
<213> ORGANISM: Homo sapiens

<400> SEQUENCE: 56
atcagttcat ttctgtgctg                                          20

<210> SEQ ID NO 57
<211> LENGTH: 20
```

```
<212> TYPE: DNA
<213> ORGANISM: Homo sapiens

<400> SEQUENCE: 57
ggcaaaccac tgatatcttc                                              20

<210> SEQ ID NO 58
<211> LENGTH: 20
<212> TYPE: DNA
<213> ORGANISM: Homo sapiens

<400> SEQUENCE: 58
atggttatta ccagggaagg                                              20

<210> SEQ ID NO 59
<211> LENGTH: 20
<212> TYPE: DNA
<213> ORGANISM: Homo sapiens

<400> SEQUENCE: 59
ttcttgtgtg taacccattg                                              20

<210> SEQ ID NO 60
<211> LENGTH: 20
<212> TYPE: DNA
<213> ORGANISM: Homo sapiens

<400> SEQUENCE: 60
tgaagtctaa acaagggagg                                              20

<210> SEQ ID NO 61
<211> LENGTH: 20
<212> TYPE: DNA
<213> ORGANISM: Homo sapiens

<400> SEQUENCE: 61
gtccactgaa taaaggcaag                                              20

<210> SEQ ID NO 62
<211> LENGTH: 20
<212> TYPE: DNA
<213> ORGANISM: Homo sapiens

<400> SEQUENCE: 62
tatgggcatc ttctctcttc                                              20

<210> SEQ ID NO 63
<211> LENGTH: 20
<212> TYPE: DNA
<213> ORGANISM: Homo sapiens

<400> SEQUENCE: 63
aaagactttc cttcatgtgg                                              20

<210> SEQ ID NO 64
<211> LENGTH: 20
<212> TYPE: DNA
<213> ORGANISM: Homo sapiens

<400> SEQUENCE: 64
aagcatggga gaacagttag                                              20

<210> SEQ ID NO 65
```

<211> LENGTH: 20
<212> TYPE: DNA
<213> ORGANISM: Homo sapiens

<400> SEQUENCE: 65
tactttatgc agcagtcagg         20

<210> SEQ ID NO 66
<211> LENGTH: 20
<212> TYPE: DNA
<213> ORGANISM: Homo sapiens

<400> SEQUENCE: 66
ccaaattgct gggattatag         20

<210> SEQ ID NO 67
<211> LENGTH: 21
<212> TYPE: DNA
<213> ORGANISM: Homo sapiens

<400> SEQUENCE: 67
ccctgggact atagatttag c       21

<210> SEQ ID NO 68
<211> LENGTH: 20
<212> TYPE: DNA
<213> ORGANISM: Homo sapiens

<400> SEQUENCE: 68
ctctttgcgt cttaggagtc         20

<210> SEQ ID NO 69
<211> LENGTH: 20
<212> TYPE: DNA
<213> ORGANISM: Homo sapiens

<400> SEQUENCE: 69
tgcagagact gatctttgag         20

<210> SEQ ID NO 70
<211> LENGTH: 20
<212> TYPE: DNA
<213> ORGANISM: Homo sapiens

<400> SEQUENCE: 70
tctcataatg tcgttgttgg         20

<210> SEQ ID NO 71
<211> LENGTH: 22
<212> TYPE: DNA
<213> ORGANISM: Homo sapiens

<400> SEQUENCE: 71
ttgatcctaa atttgacaca tc      22

<210> SEQ ID NO 72
<211> LENGTH: 20
<212> TYPE: DNA
<213> ORGANISM: Homo sapiens

<400> SEQUENCE: 72
aaagtgctga gattacaggc         20

```
<210> SEQ ID NO 73
<211> LENGTH: 20
<212> TYPE: DNA
<213> ORGANISM: Homo sapiens

<400> SEQUENCE: 73
gcaacgtgct gtagactatg                                              20

<210> SEQ ID NO 74
<211> LENGTH: 20
<212> TYPE: DNA
<213> ORGANISM: Homo sapiens

<400> SEQUENCE: 74
caagcatttg aaatatgcag                                              20

<210> SEQ ID NO 75
<211> LENGTH: 20
<212> TYPE: DNA
<213> ORGANISM: Homo sapiens

<400> SEQUENCE: 75
ttagttctga tggttctccc                                              20

<210> SEQ ID NO 76
<211> LENGTH: 20
<212> TYPE: DNA
<213> ORGANISM: Homo sapiens

<400> SEQUENCE: 76
tataggagcc attggatttc                                              20

<210> SEQ ID NO 77
<211> LENGTH: 20
<212> TYPE: DNA
<213> ORGANISM: Homo sapiens

<400> SEQUENCE: 77
atctgaaatc caagatgctg                                              20

<210> SEQ ID NO 78
<211> LENGTH: 20
<212> TYPE: DNA
<213> ORGANISM: Homo sapiens

<400> SEQUENCE: 78
tcccaaagta ctgggattac                                              20

<210> SEQ ID NO 79
<211> LENGTH: 21
<212> TYPE: DNA
<213> ORGANISM: Homo sapiens

<400> SEQUENCE: 79
atttcttatc tgaaggcact g                                            21

<210> SEQ ID NO 80
<211> LENGTH: 20
<212> TYPE: DNA
<213> ORGANISM: Homo sapiens

<400> SEQUENCE: 80
taccaaagac ccttatcagc                                              20
```

```
<210> SEQ ID NO 81
<211> LENGTH: 21
<212> TYPE: DNA
<213> ORGANISM: Homo sapiens

<400> SEQUENCE: 81
tgtctcaaag aaattgaggt c                                              21

<210> SEQ ID NO 82
<211> LENGTH: 20
<212> TYPE: DNA
<213> ORGANISM: Homo sapiens

<400> SEQUENCE: 82
taagtgcctc ttgggtagag                                                20

<210> SEQ ID NO 83
<211> LENGTH: 20
<212> TYPE: DNA
<213> ORGANISM: Homo sapiens

<400> SEQUENCE: 83
gtcttactct gtcacccagg                                                20

<210> SEQ ID NO 84
<211> LENGTH: 20
<212> TYPE: DNA
<213> ORGANISM: Homo sapiens

<400> SEQUENCE: 84
tcagagaatc acaagagcag                                                20

<210> SEQ ID NO 85
<211> LENGTH: 20
<212> TYPE: DNA
<213> ORGANISM: Homo sapiens

<400> SEQUENCE: 85
ctttataatg cgagggtctg                                                20

<210> SEQ ID NO 86
<211> LENGTH: 20
<212> TYPE: DNA
<213> ORGANISM: Homo sapiens

<400> SEQUENCE: 86
gtagtaattc cagcgagagg                                                20

<210> SEQ ID NO 87
<211> LENGTH: 20
<212> TYPE: DNA
<213> ORGANISM: Homo sapiens

<400> SEQUENCE: 87
tttaactcaa gactgcctcc                                                20

<210> SEQ ID NO 88
<211> LENGTH: 20
<212> TYPE: DNA
<213> ORGANISM: Homo sapiens

<400> SEQUENCE: 88
acatggtgaa ccagagtttc                                                20
```

<210> SEQ ID NO 89
<211> LENGTH: 20
<212> TYPE: DNA
<213> ORGANISM: Homo sapiens

<400> SEQUENCE: 89
gtccagagac ctttctaacg                                       20

<210> SEQ ID NO 90
<211> LENGTH: 20
<212> TYPE: DNA
<213> ORGANISM: Homo sapiens

<400> SEQUENCE: 90
agagtctgga tcaccttctg                                       20

<210> SEQ ID NO 91
<211> LENGTH: 20
<212> TYPE: DNA
<213> ORGANISM: Homo sapiens

<400> SEQUENCE: 91
aacttgaaca gctacggaac                                       20

<210> SEQ ID NO 92
<211> LENGTH: 20
<212> TYPE: DNA
<213> ORGANISM: Homo sapiens

<400> SEQUENCE: 92
agcgagttca aagcaaactt                                       20

<210> SEQ ID NO 93
<211> LENGTH: 20
<212> TYPE: DNA
<213> ORGANISM: Homo sapiens

<400> SEQUENCE: 93
agagcttgag aagagccaat                                       20

<210> SEQ ID NO 94
<211> LENGTH: 20
<212> TYPE: DNA
<213> ORGANISM: Homo sapiens

<400> SEQUENCE: 94
atttcttcca gatgtcctcg                                       20

<210> SEQ ID NO 95
<211> LENGTH: 20
<212> TYPE: DNA
<213> ORGANISM: Homo sapiens

<400> SEQUENCE: 95
gagtggaatg accaggttag                                       20

<210> SEQ ID NO 96
<211> LENGTH: 20
<212> TYPE: DNA
<213> ORGANISM: Homo sapiens

<400> SEQUENCE: 96

```
agggtagaga ggctatttcc                                               20

<210> SEQ ID NO 97
<211> LENGTH: 20
<212> TYPE: DNA
<213> ORGANISM: Homo sapiens

<400> SEQUENCE: 97
agaagaactt caaacttgcc                                               20

<210> SEQ ID NO 98
<211> LENGTH: 20
<212> TYPE: DNA
<213> ORGANISM: Homo sapiens

<400> SEQUENCE: 98
taaaggtttc caactccttg                                               20

<210> SEQ ID NO 99
<211> LENGTH: 20
<212> TYPE: DNA
<213> ORGANISM: Homo sapiens

<400> SEQUENCE: 99
ccaggaagtt gtgattcttc                                               20

<210> SEQ ID NO 100
<211> LENGTH: 20
<212> TYPE: DNA
<213> ORGANISM: Homo sapiens

<400> SEQUENCE: 100
tttttatgga aatcaggagg                                               20

<210> SEQ ID NO 101
<211> LENGTH: 20
<212> TYPE: DNA
<213> ORGANISM: Homo sapiens

<400> SEQUENCE: 101
gttaataata tcccccgagc                                               20

<210> SEQ ID NO 102
<211> LENGTH: 20
<212> TYPE: DNA
<213> ORGANISM: Homo sapiens

<400> SEQUENCE: 102
ctgtctgtgt ttgagctgtc                                               20

<210> SEQ ID NO 103
<211> LENGTH: 20
<212> TYPE: DNA
<213> ORGANISM: Homo sapiens

<400> SEQUENCE: 103
agcttgtaca caaaaggagg                                               20

<210> SEQ ID NO 104
<211> LENGTH: 20
<212> TYPE: DNA
<213> ORGANISM: Homo sapiens

<400> SEQUENCE: 104
```

-continued ctcgagtttg actcgctaca					20

<210> SEQ ID NO 105
<211> LENGTH: 20
<212> TYPE: DNA
<213> ORGANISM: Homo sapiens

<400> SEQUENCE: 105
agatgctgct tgagaacgag					20

<210> SEQ ID NO 106
<211> LENGTH: 20
<212> TYPE: DNA
<213> ORGANISM: Homo sapiens

<400> SEQUENCE: 106
acatctatgt tgatggaccc					20

<210> SEQ ID NO 107
<211> LENGTH: 20
<212> TYPE: DNA
<213> ORGANISM: Homo sapiens

<400> SEQUENCE: 107
ttggtaaaga atgagaaggc					20

<210> SEQ ID NO 108
<211> LENGTH: 20
<212> TYPE: DNA
<213> ORGANISM: Homo sapiens

<400> SEQUENCE: 108
gttccaagtt tccaaacaac					20

<210> SEQ ID NO 109
<211> LENGTH: 20
<212> TYPE: DNA
<213> ORGANISM: Homo sapiens

<400> SEQUENCE: 109
agaactgggt aaatgcaaag					20

<210> SEQ ID NO 110
<211> LENGTH: 20
<212> TYPE: DNA
<213> ORGANISM: Homo sapiens

<400> SEQUENCE: 110
aaaaattaag ggcagggcta					20

<210> SEQ ID NO 111
<211> LENGTH: 20
<212> TYPE: DNA
<213> ORGANISM: Homo sapiens

<400> SEQUENCE: 111
aaattcaatc cctcctcttc					20

<210> SEQ ID NO 112
<211> LENGTH: 20
<212> TYPE: DNA
<213> ORGANISM: Homo sapiens

```
<400> SEQUENCE: 112
ggaacatttc tgtcttggag                                              20

<210> SEQ ID NO 113
<211> LENGTH: 27
<212> TYPE: DNA
<213> ORGANISM: Homo sapiens

<400> SEQUENCE: 113
gtaatcatgt aatagtgttg tataggg                                      27

<210> SEQ ID NO 114
<211> LENGTH: 20
<212> TYPE: DNA
<213> ORGANISM: Homo sapiens

<400> SEQUENCE: 114
ttaggtatct tctggcttcc                                              20

<210> SEQ ID NO 115
<211> LENGTH: 20
<212> TYPE: DNA
<213> ORGANISM: Homo sapiens

<400> SEQUENCE: 115
ttacctcctt gaaggtcttg                                              20

<210> SEQ ID NO 116
<211> LENGTH: 21
<212> TYPE: DNA
<213> ORGANISM: Homo sapiens

<400> SEQUENCE: 116
cttgaattct tgatgatggt c                                            21

<210> SEQ ID NO 117
<211> LENGTH: 20
<212> TYPE: DNA
<213> ORGANISM: Homo sapiens

<400> SEQUENCE: 117
attctggaag acataaacgc                                              20

<210> SEQ ID NO 118
<211> LENGTH: 20
<212> TYPE: DNA
<213> ORGANISM: Homo sapiens

<400> SEQUENCE: 118
cagtgctaag ccatgtgtag                                              20

<210> SEQ ID NO 119
<211> LENGTH: 20
<212> TYPE: DNA
<213> ORGANISM: Homo sapiens

<400> SEQUENCE: 119
gtatatttcc tccctgtccc                                              20

<210> SEQ ID NO 120
<211> LENGTH: 20
<212> TYPE: DNA
<213> ORGANISM: Homo sapiens
```

-continued

```
<400> SEQUENCE: 120
caaagtgctg ggaatatagg                                               20

<210> SEQ ID NO 121
<211> LENGTH: 20
<212> TYPE: DNA
<213> ORGANISM: Homo sapiens

<400> SEQUENCE: 121
atgagtggag ctaggtatgg                                               20

<210> SEQ ID NO 122
<211> LENGTH: 20
<212> TYPE: DNA
<213> ORGANISM: Homo sapiens

<400> SEQUENCE: 122
cccaaccaag taaagtaagc                                               20

<210> SEQ ID NO 123
<211> LENGTH: 20
<212> TYPE: DNA
<213> ORGANISM: Homo sapiens

<400> SEQUENCE: 123
gaattcacca gctgaggtag                                               20

<210> SEQ ID NO 124
<211> LENGTH: 21
<212> TYPE: DNA
<213> ORGANISM: Homo sapiens

<400> SEQUENCE: 124
tgtttatacc tgtgtgtctg g                                             21

<210> SEQ ID NO 125
<211> LENGTH: 20
<212> TYPE: DNA
<213> ORGANISM: Homo sapiens

<400> SEQUENCE: 125
agttctcagt acttcagccg                                               20

<210> SEQ ID NO 126
<211> LENGTH: 20
<212> TYPE: DNA
<213> ORGANISM: Homo sapiens

<400> SEQUENCE: 126
atagtggcct atgtctccac                                               20

<210> SEQ ID NO 127
<211> LENGTH: 20
<212> TYPE: DNA
<213> ORGANISM: Homo sapiens

<400> SEQUENCE: 127
cggtctaata gcataccagg                                               20

<210> SEQ ID NO 128
<211> LENGTH: 20
<212> TYPE: DNA
```

<213> ORGANISM: Homo sapiens

<400> SEQUENCE: 128
aggagtatct tctcccatcc                                        20

<210> SEQ ID NO 129
<211> LENGTH: 20
<212> TYPE: DNA
<213> ORGANISM: Homo sapiens

<400> SEQUENCE: 129
cacagtacac ctggttcttg                                        20

<210> SEQ ID NO 130
<211> LENGTH: 20
<212> TYPE: DNA
<213> ORGANISM: Homo sapiens

<400> SEQUENCE: 130
gtaatgatgg atcagaaggc                                        20

<210> SEQ ID NO 131
<211> LENGTH: 20
<212> TYPE: DNA
<213> ORGANISM: Homo sapiens

<400> SEQUENCE: 131
gatattacct cattggctgg                                        20

<210> SEQ ID NO 132
<211> LENGTH: 20
<212> TYPE: DNA
<213> ORGANISM: Homo sapiens

<400> SEQUENCE: 132
taattgcact ctttcttggg                                        20

<210> SEQ ID NO 133
<211> LENGTH: 20
<212> TYPE: DNA
<213> ORGANISM: Homo sapiens

<400> SEQUENCE: 133
ttctaaggag aaggcatttg                                        20

<210> SEQ ID NO 134
<211> LENGTH: 20
<212> TYPE: DNA
<213> ORGANISM: Homo sapiens

<400> SEQUENCE: 134
gctaaagtga cttccagagg                                        20

<210> SEQ ID NO 135
<211> LENGTH: 20
<212> TYPE: DNA
<213> ORGANISM: Homo sapiens

<400> SEQUENCE: 135
taagatggga tctcaggaac                                        20

<210> SEQ ID NO 136
<211> LENGTH: 20

```
<212> TYPE: DNA
<213> ORGANISM: Homo sapiens

<400> SEQUENCE: 136
attctggaga catggagtgt                                                 20

<210> SEQ ID NO 137
<211> LENGTH: 20
<212> TYPE: DNA
<213> ORGANISM: Homo sapiens

<400> SEQUENCE: 137
ttgaggtctt gagggaatag                                                 20

<210> SEQ ID NO 138
<211> LENGTH: 20
<212> TYPE: DNA
<213> ORGANISM: Homo sapiens

<400> SEQUENCE: 138
tttcagtaag ctgtgtggtg                                                 20

<210> SEQ ID NO 139
<211> LENGTH: 20
<212> TYPE: DNA
<213> ORGANISM: Homo sapiens

<400> SEQUENCE: 139
gacctgaatc ccatattgag                                                 20

<210> SEQ ID NO 140
<211> LENGTH: 20
<212> TYPE: DNA
<213> ORGANISM: Homo sapiens

<400> SEQUENCE: 140
ctgattattt ccagacccac                                                 20

<210> SEQ ID NO 141
<211> LENGTH: 20
<212> TYPE: DNA
<213> ORGANISM: Homo sapiens

<400> SEQUENCE: 141
aaatccgaaa acttccattg                                                 20

<210> SEQ ID NO 142
<211> LENGTH: 20
<212> TYPE: DNA
<213> ORGANISM: Homo sapiens

<400> SEQUENCE: 142
actcctgctg tctacctctc                                                 20

<210> SEQ ID NO 143
<211> LENGTH: 20
<212> TYPE: DNA
<213> ORGANISM: Homo sapiens

<400> SEQUENCE: 143
agttctttga tccagaggtg                                                 20

<210> SEQ ID NO 144
```

-continued

```
<211> LENGTH: 20
<212> TYPE: DNA
<213> ORGANISM: Homo sapiens

<400> SEQUENCE: 144
aggagagatg gttgagagga                                                    20

<210> SEQ ID NO 145
<211> LENGTH: 20
<212> TYPE: DNA
<213> ORGANISM: Homo sapiens

<400> SEQUENCE: 145
gctaccaagt gcctgttctt                                                    20

<210> SEQ ID NO 146
<211> LENGTH: 20
<212> TYPE: DNA
<213> ORGANISM: Homo sapiens

<400> SEQUENCE: 146
ttcctcatgg tgtcctggta                                                    20

<210> SEQ ID NO 147
<211> LENGTH: 20
<212> TYPE: DNA
<213> ORGANISM: Homo sapiens

<400> SEQUENCE: 147
actgctcaag atttgtttcc                                                    20

<210> SEQ ID NO 148
<211> LENGTH: 20
<212> TYPE: DNA
<213> ORGANISM: Homo sapiens

<400> SEQUENCE: 148
tacacagatt tgtcaatgcc                                                    20

<210> SEQ ID NO 149
<211> LENGTH: 20
<212> TYPE: DNA
<213> ORGANISM: Homo sapiens

<400> SEQUENCE: 149
gaaaacccat ttgaatcacc                                                    20

<210> SEQ ID NO 150
<211> LENGTH: 20
<212> TYPE: DNA
<213> ORGANISM: Homo sapiens

<400> SEQUENCE: 150
tgttaagaaa agtcgaagcg                                                    20

<210> SEQ ID NO 151
<211> LENGTH: 20
<212> TYPE: DNA
<213> ORGANISM: Homo sapiens

<400> SEQUENCE: 151
ttctggaacc agatcttgac                                                    20
```

```
<210> SEQ ID NO 152
<211> LENGTH: 20
<212> TYPE: DNA
<213> ORGANISM: Homo sapiens

<400> SEQUENCE: 152
gaaactacaa ttcccagcag                                              20

<210> SEQ ID NO 153
<211> LENGTH: 20
<212> TYPE: DNA
<213> ORGANISM: Homo sapiens

<400> SEQUENCE: 153
tctctctcct tgtctgttcc                                              20

<210> SEQ ID NO 154
<211> LENGTH: 20
<212> TYPE: DNA
<213> ORGANISM: Homo sapiens

<400> SEQUENCE: 154
gatagggtga aagaatggtg                                              20

<210> SEQ ID NO 155
<211> LENGTH: 20
<212> TYPE: DNA
<213> ORGANISM: Homo sapiens

<400> SEQUENCE: 155
gcttcaagga gatttagcag                                              20

<210> SEQ ID NO 156
<211> LENGTH: 20
<212> TYPE: DNA
<213> ORGANISM: Homo sapiens

<400> SEQUENCE: 156
gtttgaaatt ggatgtaccc                                              20

<210> SEQ ID NO 157
<211> LENGTH: 20
<212> TYPE: DNA
<213> ORGANISM: Homo sapiens

<400> SEQUENCE: 157
gaggcaaatt atcctgtttg                                              20

<210> SEQ ID NO 158
<211> LENGTH: 20
<212> TYPE: DNA
<213> ORGANISM: Homo sapiens

<400> SEQUENCE: 158
aagactggca tttctacctg                                              20

<210> SEQ ID NO 159
<211> LENGTH: 20
<212> TYPE: DNA
<213> ORGANISM: Homo sapiens

<400> SEQUENCE: 159
gtgtggttct aattgcattg                                              20
```

```
<210> SEQ ID NO 160
<211> LENGTH: 20
<212> TYPE: DNA
<213> ORGANISM: Homo sapiens

<400> SEQUENCE: 160
gggaaaggat cataatgttg                                              20

<210> SEQ ID NO 161
<211> LENGTH: 20
<212> TYPE: DNA
<213> ORGANISM: Homo sapiens

<400> SEQUENCE: 161
tgcctttatc tgcttagacc                                              20

<210> SEQ ID NO 162
<211> LENGTH: 20
<212> TYPE: DNA
<213> ORGANISM: Homo sapiens

<400> SEQUENCE: 162
aaacttcaaa gttctagcgg                                              20

<210> SEQ ID NO 163
<211> LENGTH: 20
<212> TYPE: DNA
<213> ORGANISM: Homo sapiens

<400> SEQUENCE: 163
aggagcagat atgtcagagg                                              20

<210> SEQ ID NO 164
<211> LENGTH: 20
<212> TYPE: DNA
<213> ORGANISM: Homo sapiens

<400> SEQUENCE: 164
gacatcttcc cagacagcac                                              20

<210> SEQ ID NO 165
<211> LENGTH: 20
<212> TYPE: DNA
<213> ORGANISM: Homo sapiens

<400> SEQUENCE: 165
tctaggagca gtggaagaag                                              20

<210> SEQ ID NO 166
<211> LENGTH: 20
<212> TYPE: DNA
<213> ORGANISM: Homo sapiens

<400> SEQUENCE: 166
tatcatctgt agcacaaccc                                              20

<210> SEQ ID NO 167
<211> LENGTH: 20
<212> TYPE: DNA
<213> ORGANISM: Homo sapiens

<400> SEQUENCE: 167
acgctactgt aaccaagagg                                              20
```

<210> SEQ ID NO 168
<211> LENGTH: 20
<212> TYPE: DNA
<213> ORGANISM: Homo sapiens

<400> SEQUENCE: 168
aacagcgcta tttcctacac                                                    20

<210> SEQ ID NO 169
<211> LENGTH: 20
<212> TYPE: DNA
<213> ORGANISM: Homo sapiens

<400> SEQUENCE: 169
agaaggtttg tgtgtgtgtg                                                    20

<210> SEQ ID NO 170
<211> LENGTH: 20
<212> TYPE: DNA
<213> ORGANISM: Homo sapiens

<400> SEQUENCE: 170
cagcaaacaa tgtgaaagag                                                    20

<210> SEQ ID NO 171
<211> LENGTH: 20
<212> TYPE: DNA
<213> ORGANISM: Homo sapiens

<400> SEQUENCE: 171
actactatga tgctacgccc                                                    20

<210> SEQ ID NO 172
<211> LENGTH: 24
<212> TYPE: DNA
<213> ORGANISM: Homo sapiens

<400> SEQUENCE: 172
gatttggagt ctctttaaat tagc                                               24

<210> SEQ ID NO 173
<211> LENGTH: 20
<212> TYPE: DNA
<213> ORGANISM: Homo sapiens

<400> SEQUENCE: 173
tctcgataca cacaacatcc                                                    20

<210> SEQ ID NO 174
<211> LENGTH: 20
<212> TYPE: DNA
<213> ORGANISM: Homo sapiens

<400> SEQUENCE: 174
agcctgcaaa ttattctctg                                                    20

<210> SEQ ID NO 175
<211> LENGTH: 20
<212> TYPE: DNA
<213> ORGANISM: Homo sapiens

<400> SEQUENCE: 175
ctctgctgag gcgagtacgg                                              20

<210> SEQ ID NO 176
<211> LENGTH: 20
<212> TYPE: DNA
<213> ORGANISM: Homo sapiens

<400> SEQUENCE: 176
attcttgggg gatattcctt                                              20

<210> SEQ ID NO 177
<211> LENGTH: 20
<212> TYPE: DNA
<213> ORGANISM: Homo sapiens

<400> SEQUENCE: 177
tcttatccta ttgcctgagc                                              20

<210> SEQ ID NO 178
<211> LENGTH: 20
<212> TYPE: DNA
<213> ORGANISM: Homo sapiens

<400> SEQUENCE: 178
acatagctca cctcataggc                                              20

<210> SEQ ID NO 179
<211> LENGTH: 20
<212> TYPE: DNA
<213> ORGANISM: Homo sapiens

<400> SEQUENCE: 179
agtacctgct cctcaccatc                                              20

<210> SEQ ID NO 180
<211> LENGTH: 20
<212> TYPE: DNA
<213> ORGANISM: Homo sapiens

<400> SEQUENCE: 180
cacgcttaac aatgtaatgg                                              20

<210> SEQ ID NO 181
<211> LENGTH: 20
<212> TYPE: DNA
<213> ORGANISM: Homo sapiens

<400> SEQUENCE: 181
attctgggaa ggagtctacc                                              20

<210> SEQ ID NO 182
<211> LENGTH: 20
<212> TYPE: DNA
<213> ORGANISM: Homo sapiens

<400> SEQUENCE: 182
ggttctcaaa taatatgccg                                              20

<210> SEQ ID NO 183
<211> LENGTH: 20
<212> TYPE: DNA
<213> ORGANISM: Homo sapiens

<400> SEQUENCE: 183

```
tccttacaca tggtcctacc                                               20

<210> SEQ ID NO 184
<211> LENGTH: 20
<212> TYPE: DNA
<213> ORGANISM: Homo sapiens

<400> SEQUENCE: 184
ttctcttcct gaagctcttg                                               20

<210> SEQ ID NO 185
<211> LENGTH: 20
<212> TYPE: DNA
<213> ORGANISM: Homo sapiens

<400> SEQUENCE: 185
gtaaactgtg cctgctgtag                                               20

<210> SEQ ID NO 186
<211> LENGTH: 20
<212> TYPE: DNA
<213> ORGANISM: Homo sapiens

<400> SEQUENCE: 186
atttctcaca ataccttggg                                               20

<210> SEQ ID NO 187
<211> LENGTH: 20
<212> TYPE: DNA
<213> ORGANISM: Homo sapiens

<400> SEQUENCE: 187
tgggaaacag atctctaagg                                               20

<210> SEQ ID NO 188
<211> LENGTH: 20
<212> TYPE: DNA
<213> ORGANISM: Homo sapiens

<400> SEQUENCE: 188
gcctgtaatt ccagctactc                                               20

<210> SEQ ID NO 189
<211> LENGTH: 20
<212> TYPE: DNA
<213> ORGANISM: Homo sapiens

<400> SEQUENCE: 189
tgacaaatca cacaaggttc                                               20

<210> SEQ ID NO 190
<211> LENGTH: 20
<212> TYPE: DNA
<213> ORGANISM: Homo sapiens

<400> SEQUENCE: 190
agttggtgta aaggatgagc                                               20

<210> SEQ ID NO 191
<211> LENGTH: 20
<212> TYPE: DNA
<213> ORGANISM: Homo sapiens
```

```
<400> SEQUENCE: 191
gctagatcat gacactgcac                                               20

<210> SEQ ID NO 192
<211> LENGTH: 22
<212> TYPE: DNA
<213> ORGANISM: Homo sapiens

<400> SEQUENCE: 192
tgaggtgagt agatcacttg ag                                            22

<210> SEQ ID NO 193
<211> LENGTH: 20
<212> TYPE: DNA
<213> ORGANISM: Homo sapiens

<400> SEQUENCE: 193
tttgtcttac gggtaaatgg                                               20

<210> SEQ ID NO 194
<211> LENGTH: 20
<212> TYPE: DNA
<213> ORGANISM: Homo sapiens

<400> SEQUENCE: 194
gcttgagagg aagtcaagag                                               20

<210> SEQ ID NO 195
<211> LENGTH: 20
<212> TYPE: DNA
<213> ORGANISM: Homo sapiens

<400> SEQUENCE: 195
acagaatgct ttagtccacc                                               20

<210> SEQ ID NO 196
<211> LENGTH: 20
<212> TYPE: DNA
<213> ORGANISM: Homo sapiens

<400> SEQUENCE: 196
gtaatcacct ttcatcggag                                               20

<210> SEQ ID NO 197
<211> LENGTH: 20
<212> TYPE: DNA
<213> ORGANISM: Homo sapiens

<400> SEQUENCE: 197
agcttgttct accaggaatg                                               20

<210> SEQ ID NO 198
<211> LENGTH: 20
<212> TYPE: DNA
<213> ORGANISM: Homo sapiens

<400> SEQUENCE: 198
ctctcaataa atggccaaag                                               20

<210> SEQ ID NO 199
<211> LENGTH: 20
<212> TYPE: DNA
<213> ORGANISM: Homo sapiens
```

```
<400> SEQUENCE: 199
aaagagattc tgcttggttg                                               20

<210> SEQ ID NO 200
<211> LENGTH: 20
<212> TYPE: DNA
<213> ORGANISM: Homo sapiens

<400> SEQUENCE: 200
cccataaaca tgttgaatcc                                               20

<210> SEQ ID NO 201
<211> LENGTH: 20
<212> TYPE: DNA
<213> ORGANISM: Homo sapiens

<400> SEQUENCE: 201
tgcaacatca ttctctcaag                                               20

<210> SEQ ID NO 202
<211> LENGTH: 20
<212> TYPE: DNA
<213> ORGANISM: Homo sapiens

<400> SEQUENCE: 202
accattcacg atcacttagg                                               20

<210> SEQ ID NO 203
<211> LENGTH: 20
<212> TYPE: DNA
<213> ORGANISM: Homo sapiens

<400> SEQUENCE: 203
aagcagaacc acttgaacac                                               20

<210> SEQ ID NO 204
<211> LENGTH: 20
<212> TYPE: DNA
<213> ORGANISM: Homo sapiens

<400> SEQUENCE: 204
ttcacaatgc cattaacaac                                               20

<210> SEQ ID NO 205
<211> LENGTH: 20
<212> TYPE: DNA
<213> ORGANISM: Homo sapiens

<400> SEQUENCE: 205
gagatgtggg attgtaggac                                               20

<210> SEQ ID NO 206
<211> LENGTH: 20
<212> TYPE: DNA
<213> ORGANISM: Homo sapiens

<400> SEQUENCE: 206
acgtcgactt taggtttgtc                                               20

<210> SEQ ID NO 207
<211> LENGTH: 20
<212> TYPE: DNA
```

```
<213> ORGANISM: Homo sapiens

<400> SEQUENCE: 207
cataattcac tgcagctttg                                               20

<210> SEQ ID NO 208
<211> LENGTH: 20
<212> TYPE: DNA
<213> ORGANISM: Homo sapiens

<400> SEQUENCE: 208
gtcaggagac tgagaccatc                                               20

<210> SEQ ID NO 209
<211> LENGTH: 20
<212> TYPE: DNA
<213> ORGANISM: Homo sapiens

<400> SEQUENCE: 209
tgcctcatag gctacctaac                                               20

<210> SEQ ID NO 210
<211> LENGTH: 20
<212> TYPE: DNA
<213> ORGANISM: Homo sapiens

<400> SEQUENCE: 210
gagacatatc aaccaaaggc                                               20

<210> SEQ ID NO 211
<211> LENGTH: 20
<212> TYPE: DNA
<213> ORGANISM: Homo sapiens

<400> SEQUENCE: 211
agaagtgcta catcccaaag                                               20

<210> SEQ ID NO 212
<211> LENGTH: 20
<212> TYPE: DNA
<213> ORGANISM: Homo sapiens

<400> SEQUENCE: 212
atcctagtac tcacgggttg                                               20

<210> SEQ ID NO 213
<211> LENGTH: 20
<212> TYPE: DNA
<213> ORGANISM: Homo sapiens

<400> SEQUENCE: 213
aactgaagtt gggcatttag                                               20

<210> SEQ ID NO 214
<211> LENGTH: 20
<212> TYPE: DNA
<213> ORGANISM: Homo sapiens

<400> SEQUENCE: 214
taccttgtta gcaaagggag                                               20

<210> SEQ ID NO 215
<211> LENGTH: 20
```

```
<212> TYPE: DNA
<213> ORGANISM: Homo sapiens

<400> SEQUENCE: 215
cagaggcatt tatctcatcc                                              20

<210> SEQ ID NO 216
<211> LENGTH: 20
<212> TYPE: DNA
<213> ORGANISM: Homo sapiens

<400> SEQUENCE: 216
aagctacatg gcttcaagag                                              20

<210> SEQ ID NO 217
<211> LENGTH: 20
<212> TYPE: DNA
<213> ORGANISM: Homo sapiens

<400> SEQUENCE: 217
aaatgtgcat ggaagaaatc                                              20

<210> SEQ ID NO 218
<211> LENGTH: 20
<212> TYPE: DNA
<213> ORGANISM: Homo sapiens

<400> SEQUENCE: 218
ctataatccc agcaatttgg                                              20

<210> SEQ ID NO 219
<211> LENGTH: 20
<212> TYPE: DNA
<213> ORGANISM: Homo sapiens

<400> SEQUENCE: 219
aagacatgtt ctgacggaag                                              20

<210> SEQ ID NO 220
<211> LENGTH: 20
<212> TYPE: DNA
<213> ORGANISM: Homo sapiens

<400> SEQUENCE: 220
atgactccta agacgcaaag                                              20

<210> SEQ ID NO 221
<211> LENGTH: 20
<212> TYPE: DNA
<213> ORGANISM: Homo sapiens

<400> SEQUENCE: 221
gtggtccaag acaattcttc                                              20

<210> SEQ ID NO 222
<211> LENGTH: 20
<212> TYPE: DNA
<213> ORGANISM: Homo sapiens

<400> SEQUENCE: 222
accaacaacg acattatgag                                              20

<210> SEQ ID NO 223
```

```
<211> LENGTH: 20
<212> TYPE: DNA
<213> ORGANISM: Homo sapiens

<400> SEQUENCE: 223
gtaaagatga aattcggctc                                              20

<210> SEQ ID NO 224
<211> LENGTH: 20
<212> TYPE: DNA
<213> ORGANISM: Homo sapiens

<400> SEQUENCE: 224
gccttgcttt agtttagtgg                                              20

<210> SEQ ID NO 225
<211> LENGTH: 20
<212> TYPE: DNA
<213> ORGANISM: Homo sapiens

<400> SEQUENCE: 225
tggtaatgtg gtgtgatttc                                              20

<210> SEQ ID NO 226
<211> LENGTH: 20
<212> TYPE: DNA
<213> ORGANISM: Homo sapiens

<400> SEQUENCE: 226
attgcattga attgacacac                                              20

<210> SEQ ID NO 227
<211> LENGTH: 20
<212> TYPE: DNA
<213> ORGANISM: Homo sapiens

<400> SEQUENCE: 227
tcacgtttgg tacatgagac                                              20

<210> SEQ ID NO 228
<211> LENGTH: 20
<212> TYPE: DNA
<213> ORGANISM: Homo sapiens

<400> SEQUENCE: 228
tgctgtattc accaataacg                                              20

<210> SEQ ID NO 229
<211> LENGTH: 20
<212> TYPE: DNA
<213> ORGANISM: Homo sapiens

<400> SEQUENCE: 229
gtcaggagat caagaccatc                                              20

<210> SEQ ID NO 230
<211> LENGTH: 20
<212> TYPE: DNA
<213> ORGANISM: Homo sapiens

<400> SEQUENCE: 230
tacagcaact gctctgaaag                                              20
```

```
<210> SEQ ID NO 231
<211> LENGTH: 20
<212> TYPE: DNA
<213> ORGANISM: Homo sapiens

<400> SEQUENCE: 231
atttgctact gttgacaggg                                               20

<210> SEQ ID NO 232
<211> LENGTH: 20
<212> TYPE: DNA
<213> ORGANISM: Homo sapiens

<400> SEQUENCE: 232
catcacacac agaaaggaag                                               20

<210> SEQ ID NO 233
<211> LENGTH: 20
<212> TYPE: DNA
<213> ORGANISM: Homo sapiens

<400> SEQUENCE: 233
ttctgtaaga aggaagcctg                                               20

<210> SEQ ID NO 234
<211> LENGTH: 20
<212> TYPE: DNA
<213> ORGANISM: Homo sapiens

<400> SEQUENCE: 234
agtaatcaaa caggctctgc                                               20

<210> SEQ ID NO 235
<211> LENGTH: 20
<212> TYPE: DNA
<213> ORGANISM: Homo sapiens

<400> SEQUENCE: 235
agctacttga gaggttgagg                                               20

<210> SEQ ID NO 236
<211> LENGTH: 21
<212> TYPE: DNA
<213> ORGANISM: Homo sapiens

<400> SEQUENCE: 236
ctttcctcat ctagtgagct g                                             21

<210> SEQ ID NO 237
<211> LENGTH: 20
<212> TYPE: DNA
<213> ORGANISM: Homo sapiens

<400> SEQUENCE: 237
gatggatttc ttcaggattg                                               20

<210> SEQ ID NO 238
<211> LENGTH: 20
<212> TYPE: DNA
<213> ORGANISM: Homo sapiens

<400> SEQUENCE: 238
ttgtaagttc cagtgcaaag                                               20
```

```
<210> SEQ ID NO 239
<211> LENGTH: 20
<212> TYPE: DNA
<213> ORGANISM: Homo sapiens

<400> SEQUENCE: 239
atttaggcat tcgactcatc                                               20

<210> SEQ ID NO 240
<211> LENGTH: 20
<212> TYPE: DNA
<213> ORGANISM: Homo sapiens

<400> SEQUENCE: 240
tacagtcctg gatgatgatg                                               20

<210> SEQ ID NO 241
<211> LENGTH: 20
<212> TYPE: DNA
<213> ORGANISM: Homo sapiens

<400> SEQUENCE: 241
tccagatctg ctatctctcc                                               20

<210> SEQ ID NO 242
<211> LENGTH: 20
<212> TYPE: DNA
<213> ORGANISM: Homo sapiens

<400> SEQUENCE: 242
tgatctgtct caggactctg                                               20

<210> SEQ ID NO 243
<211> LENGTH: 20
<212> TYPE: DNA
<213> ORGANISM: Homo sapiens

<400> SEQUENCE: 243
tttgatcatg catttgaaac                                               20

<210> SEQ ID NO 244
<211> LENGTH: 21
<212> TYPE: DNA
<213> ORGANISM: Homo sapiens

<400> SEQUENCE: 244
tcacaactta agatttggct c                                             21

<210> SEQ ID NO 245
<211> LENGTH: 20
<212> TYPE: DNA
<213> ORGANISM: Homo sapiens

<400> SEQUENCE: 245
gcgacgagat ataaggcagt                                               20

<210> SEQ ID NO 246
<211> LENGTH: 20
<212> TYPE: DNA
<213> ORGANISM: Homo sapiens

<400> SEQUENCE: 246
tttctacgac tatgactgcg                                               20
```

```
<210> SEQ ID NO 247
<211> LENGTH: 20
<212> TYPE: DNA
<213> ORGANISM: Homo sapiens

<400> SEQUENCE: 247
aagtttgctt tgaactcgct                                               20

<210> SEQ ID NO 248
<211> LENGTH: 20
<212> TYPE: DNA
<213> ORGANISM: Homo sapiens

<400> SEQUENCE: 248
atggtttctt tctgaggttg                                               20

<210> SEQ ID NO 249
<211> LENGTH: 20
<212> TYPE: DNA
<213> ORGANISM: Homo sapiens

<400> SEQUENCE: 249
tttgaagttc ttctggaacc                                               20

<210> SEQ ID NO 250
<211> LENGTH: 20
<212> TYPE: DNA
<213> ORGANISM: Homo sapiens

<400> SEQUENCE: 250
cattgaccat tacctcactg                                               20

<210> SEQ ID NO 251
<211> LENGTH: 20
<212> TYPE: DNA
<213> ORGANISM: Homo sapiens

<400> SEQUENCE: 251
aataaaggct tgcattcttg                                               20

<210> SEQ ID NO 252
<211> LENGTH: 20
<212> TYPE: DNA
<213> ORGANISM: Homo sapiens

<400> SEQUENCE: 252
tttccttctt gctaatgtcc                                               20

<210> SEQ ID NO 253
<211> LENGTH: 20
<212> TYPE: DNA
<213> ORGANISM: Homo sapiens

<400> SEQUENCE: 253
acccagagat ggttttgttt                                               20

<210> SEQ ID NO 254
<211> LENGTH: 20
<212> TYPE: DNA
<213> ORGANISM: Homo sapiens

<400> SEQUENCE: 254
```
acagctcaaa cacagacaga                                               20

<210> SEQ ID NO 255
<211> LENGTH: 20
<212> TYPE: DNA
<213> ORGANISM: Homo sapiens

<400> SEQUENCE: 255
aacaacagac acccatatcc                                               20

<210> SEQ ID NO 256
<211> LENGTH: 20
<212> TYPE: DNA
<213> ORGANISM: Homo sapiens

<400> SEQUENCE: 256
caaacttctt ccagatgtcc                                               20

<210> SEQ ID NO 257
<211> LENGTH: 20
<212> TYPE: DNA
<213> ORGANISM: Homo sapiens

<400> SEQUENCE: 257
gttcacggga aagggaaga                                                20

<210> SEQ ID NO 258
<211> LENGTH: 20
<212> TYPE: DNA
<213> ORGANISM: Homo sapiens

<400> SEQUENCE: 258
ggtctttacc tgaatcgctc                                               20

<210> SEQ ID NO 259
<211> LENGTH: 20
<212> TYPE: DNA
<213> ORGANISM: Homo sapiens

<400> SEQUENCE: 259
ctcattcttt accaactccg                                               20

<210> SEQ ID NO 260
<211> LENGTH: 23
<212> TYPE: DNA
<213> ORGANISM: Homo sapiens

<400> SEQUENCE: 260
tgtcaatggt atttacagaa atg                                           23

<210> SEQ ID NO 261
<211> LENGTH: 20
<212> TYPE: DNA
<213> ORGANISM: Homo sapiens

<400> SEQUENCE: 261
agaactttgc atttacccag                                               20

<210> SEQ ID NO 262
<211> LENGTH: 20
<212> TYPE: DNA
<213> ORGANISM: Homo sapiens

<400> SEQUENCE: 262
tgaggtctca gcttaattcc                                                   20

<210> SEQ ID NO 263
<211> LENGTH: 20
<212> TYPE: DNA
<213> ORGANISM: Homo sapiens

<400> SEQUENCE: 263
agcttcgtct cagctcctac                                                   20

<210> SEQ ID NO 264
<211> LENGTH: 20
<212> TYPE: DNA
<213> ORGANISM: Homo sapiens

<400> SEQUENCE: 264
aggtgatcta accacctcag                                                   20

<210> SEQ ID NO 265
<211> LENGTH: 20
<212> TYPE: DNA
<213> ORGANISM: Homo sapiens

<400> SEQUENCE: 265
acttaccacg aagtgaaacc                                                   20

<210> SEQ ID NO 266
<211> LENGTH: 20
<212> TYPE: DNA
<213> ORGANISM: Homo sapiens

<400> SEQUENCE: 266
gatctgtcac agtttctccc                                                   20

<210> SEQ ID NO 267
<211> LENGTH: 20
<212> TYPE: DNA
<213> ORGANISM: Homo sapiens

<400> SEQUENCE: 267
tacaggctac ctttcctttc                                                   20

<210> SEQ ID NO 268
<211> LENGTH: 20
<212> TYPE: DNA
<213> ORGANISM: Homo sapiens

<400> SEQUENCE: 268
atttcaggct ggcaatatac                                                   20

<210> SEQ ID NO 269
<211> LENGTH: 20
<212> TYPE: DNA
<213> ORGANISM: Homo sapiens

<400> SEQUENCE: 269
tggtaataaa gctctcaggg                                                   20

<210> SEQ ID NO 270
<211> LENGTH: 20
<212> TYPE: DNA
<213> ORGANISM: Homo sapiens

<400> SEQUENCE: 270 aacatacccca attcaaatgc                                              20

<210> SEQ ID NO 271
<211> LENGTH: 20
<212> TYPE: DNA
<213> ORGANISM: Homo sapiens

<400> SEQUENCE: 271
taaatccagg agttcgagtc                                               20

<210> SEQ ID NO 272
<211> LENGTH: 20
<212> TYPE: DNA
<213> ORGANISM: Homo sapiens

<400> SEQUENCE: 272
catcaaaccc aataaccttc                                               20

<210> SEQ ID NO 273
<211> LENGTH: 20
<212> TYPE: DNA
<213> ORGANISM: Homo sapiens

<400> SEQUENCE: 273
tcaacacaaa tacctgcaac                                               20

<210> SEQ ID NO 274
<211> LENGTH: 20
<212> TYPE: DNA
<213> ORGANISM: Homo sapiens

<400> SEQUENCE: 274
cttggaatcc tgattgctta                                               20

<210> SEQ ID NO 275
<211> LENGTH: 20
<212> TYPE: DNA
<213> ORGANISM: Homo sapiens

<400> SEQUENCE: 275
gcagtaatct tggctacctc                                               20

<210> SEQ ID NO 276
<211> LENGTH: 20
<212> TYPE: DNA
<213> ORGANISM: Homo sapiens

<400> SEQUENCE: 276
ctcttaatga cccaatctgc                                               20

<210> SEQ ID NO 277
<211> LENGTH: 20
<212> TYPE: DNA
<213> ORGANISM: Homo sapiens

<400> SEQUENCE: 277
ttaatccagt tctctgtggc                                               20

<210> SEQ ID NO 278
<211> LENGTH: 20
<212> TYPE: DNA
<213> ORGANISM: Homo sapiens

```
<400> SEQUENCE: 278
ctcccaatta tttagatggc                                            20

<210> SEQ ID NO 279
<211> LENGTH: 21
<212> TYPE: DNA
<213> ORGANISM: Homo sapiens

<400> SEQUENCE: 279
ggacacttac tcatttgaag c                                          21

<210> SEQ ID NO 280
<211> LENGTH: 20
<212> TYPE: DNA
<213> ORGANISM: Homo sapiens

<400> SEQUENCE: 280
agagttacac gagaaatgcc                                            20

<210> SEQ ID NO 281
<211> LENGTH: 20
<212> TYPE: DNA
<213> ORGANISM: Homo sapiens

<400> SEQUENCE: 281
gcgcacacac acaaatatac                                            20

<210> SEQ ID NO 282
<211> LENGTH: 20
<212> TYPE: DNA
<213> ORGANISM: Homo sapiens

<400> SEQUENCE: 282
gaagctgcat tctaagttgc                                            20

<210> SEQ ID NO 283
<211> LENGTH: 20
<212> TYPE: DNA
<213> ORGANISM: Homo sapiens

<400> SEQUENCE: 283
aaatgctgaa atcaagaagg                                            20

<210> SEQ ID NO 284
<211> LENGTH: 20
<212> TYPE: DNA
<213> ORGANISM: Homo sapiens

<400> SEQUENCE: 284
tgcatgttgt ttcataatcc                                            20

<210> SEQ ID NO 285
<211> LENGTH: 20
<212> TYPE: DNA
<213> ORGANISM: Homo sapiens

<400> SEQUENCE: 285
aactttgcag tgtttcttcc                                            20

<210> SEQ ID NO 286
<211> LENGTH: 20
<212> TYPE: DNA
```

```
<213> ORGANISM: Homo sapiens

<400> SEQUENCE: 286
taagttcttg gacttctggg                                           20

<210> SEQ ID NO 287
<211> LENGTH: 20
<212> TYPE: DNA
<213> ORGANISM: Homo sapiens

<400> SEQUENCE: 287
gagatcccat cttacaatgc                                           20

<210> SEQ ID NO 288
<211> LENGTH: 20
<212> TYPE: DNA
<213> ORGANISM: Homo sapiens

<400> SEQUENCE: 288
tctttgtcca atactgcaac                                           20

<210> SEQ ID NO 289
<211> LENGTH: 20
<212> TYPE: DNA
<213> ORGANISM: Homo sapiens

<400> SEQUENCE: 289
aaccaggaat gtgtttcact                                           20

<210> SEQ ID NO 290
<211> LENGTH: 21
<212> TYPE: DNA
<213> ORGANISM: Homo sapiens

<400> SEQUENCE: 290
accacacagc ttactgaaat c                                         21

<210> SEQ ID NO 291
<211> LENGTH: 20
<212> TYPE: DNA
<213> ORGANISM: Homo sapiens

<400> SEQUENCE: 291
agggacataa tgaaagcatc                                           20

<210> SEQ ID NO 292
<211> LENGTH: 20
<212> TYPE: DNA
<213> ORGANISM: Homo sapiens

<400> SEQUENCE: 292
gtgggtctgg aaataatcag                                           20

<210> SEQ ID NO 293
<211> LENGTH: 20
<212> TYPE: DNA
<213> ORGANISM: Homo sapiens

<400> SEQUENCE: 293
agaaatcttg agtttgcacc                                           20

<210> SEQ ID NO 294
<211> LENGTH: 20
```

<212> TYPE: DNA
<213> ORGANISM: Homo sapiens

<400> SEQUENCE: 294
gaggagaggt agacagcagg                                                  20

<210> SEQ ID NO 295
<211> LENGTH: 20
<212> TYPE: DNA
<213> ORGANISM: Homo sapiens

<400> SEQUENCE: 295
tgctcctagg aacctaattg                                                  20

<210> SEQ ID NO 296
<211> LENGTH: 20
<212> TYPE: DNA
<213> ORGANISM: Homo sapiens

<400> SEQUENCE: 296
ttccttaacc tcctttaccc                                                  20

<210> SEQ ID NO 297
<211> LENGTH: 20
<212> TYPE: DNA
<213> ORGANISM: Homo sapiens

<400> SEQUENCE: 297
actgaaaaac ccctgagctg                                                  20

<210> SEQ ID NO 298
<211> LENGTH: 20
<212> TYPE: DNA
<213> ORGANISM: Homo sapiens

<400> SEQUENCE: 298
agctacaaga aagtgggcat                                                  20

<210> SEQ ID NO 299
<211> LENGTH: 20
<212> TYPE: DNA
<213> ORGANISM: Homo sapiens

<400> SEQUENCE: 299
accagaatat ttggcaaagg                                                  20

<210> SEQ ID NO 300
<211> LENGTH: 20
<212> TYPE: DNA
<213> ORGANISM: Homo sapiens

<400> SEQUENCE: 300
tcactgacac aaaggaagtg                                                  20

<210> SEQ ID NO 301
<211> LENGTH: 20
<212> TYPE: DNA
<213> ORGANISM: Homo sapiens

<400> SEQUENCE: 301
atctttaagc agagaagggc                                                  20

<210> SEQ ID NO 302

```
<211> LENGTH: 20
<212> TYPE: DNA
<213> ORGANISM: Homo sapiens

<400> SEQUENCE: 302
ctccaccttg ctatacggtc                                              20

<210> SEQ ID NO 303
<211> LENGTH: 20
<212> TYPE: DNA
<213> ORGANISM: Homo sapiens

<400> SEQUENCE: 303
agaaccaccg ctacaaaatg                                              20

<210> SEQ ID NO 304
<211> LENGTH: 20
<212> TYPE: DNA
<213> ORGANISM: Homo sapiens

<400> SEQUENCE: 304
taatcctaat gctctgaccc                                              20

<210> SEQ ID NO 305
<211> LENGTH: 20
<212> TYPE: DNA
<213> ORGANISM: Homo sapiens

<400> SEQUENCE: 305
gagagacagg gcaatcatac                                              20

<210> SEQ ID NO 306
<211> LENGTH: 20
<212> TYPE: DNA
<213> ORGANISM: Homo sapiens

<400> SEQUENCE: 306
ttacctggaa agttctctcg                                              20

<210> SEQ ID NO 307
<211> LENGTH: 20
<212> TYPE: DNA
<213> ORGANISM: Homo sapiens

<400> SEQUENCE: 307
actgaataca gggcaaagag                                              20

<210> SEQ ID NO 308
<211> LENGTH: 20
<212> TYPE: DNA
<213> ORGANISM: Homo sapiens

<400> SEQUENCE: 308
aagacaaatg tgcctctttc                                              20

<210> SEQ ID NO 309
<211> LENGTH: 20
<212> TYPE: DNA
<213> ORGANISM: Homo sapiens

<400> SEQUENCE: 309
cagcattcac taacaaggtg                                              20
```

```
<210> SEQ ID NO 310
<211> LENGTH: 20
<212> TYPE: DNA
<213> ORGANISM: Homo sapiens

<400> SEQUENCE: 310
ttggacagaa agttaggagg                                              20

<210> SEQ ID NO 311
<211> LENGTH: 20
<212> TYPE: DNA
<213> ORGANISM: Homo sapiens

<400> SEQUENCE: 311
catgcactgg attaaatgag                                              20

<210> SEQ ID NO 312
<211> LENGTH: 20
<212> TYPE: DNA
<213> ORGANISM: Homo sapiens

<400> SEQUENCE: 312
attcctgaaa gcagtcattc                                              20

<210> SEQ ID NO 313
<211> LENGTH: 20
<212> TYPE: DNA
<213> ORGANISM: Homo sapiens

<400> SEQUENCE: 313
ctctgctggt ctttcatagc                                              20

<210> SEQ ID NO 314
<211> LENGTH: 20
<212> TYPE: DNA
<213> ORGANISM: Homo sapiens

<400> SEQUENCE: 314
tgcctttatc tgcttagacc                                              20
```